United States Patent
Hu et al.

(10) Patent No.: US 10,586,336 B2
(45) Date of Patent: Mar. 10, 2020

(54) IMAGE PRE-PROCESSING FOR ACCELERATING CYTOLOGICAL IMAGE CLASSIFICATION BY FULLY CONVOLUTIONAL NEURAL NETWORKS

(71) Applicant: Hong Kong Applied Science and Technology Research Institute Company Limited, Hong Kong (HK)

(72) Inventors: Yu Hu, Hong Kong (HK); Lu Wang, Hong Kong (HK); Ping Shun Leung, Hong Kong (HK)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 179 days.

(21) Appl. No.: 15/983,434

(22) Filed: May 18, 2018

(65) Prior Publication Data
US 2019/0355119 A1    Nov. 21, 2019

(51) Int. Cl.
*G06T 7/11*        (2017.01)
*G06N 5/04*        (2006.01)
(Continued)

(52) U.S. Cl.
CPC .................. *G06T 7/11* (2017.01); *G06K 9/66* (2013.01); *G06N 5/046* (2013.01); *G06T 7/149* (2017.01); *G06T 7/194* (2017.01); *G16H 50/20* (2018.01)

(58) Field of Classification Search
CPC .......... G06T 7/11; G06T 7/194; G06T 7/149; G06K 9/66
(Continued)

(56) References Cited

U.S. PATENT DOCUMENTS 6,690,990 B1    2/2004    Martin et al.
7,587,078 B2    9/2009    Zahniser et al.
(Continued)

FOREIGN PATENT DOCUMENTS

CN    102831607 B    4/2015
CN    107016677 A    8/2017
(Continued)

OTHER PUBLICATIONS

E. Teng et al., "ClickBAIT: Click-based Accelerated Incremental Training of Convolutional Neural Networks," arXiv:1709.05021v1, [cs.CV], Sep. 15, 2017 (Cornell University Library).
(Continued)

*Primary Examiner* — Ayodeji O Ayotunde
(74) *Attorney, Agent, or Firm* — Spruson & Ferguson (Hong Kong) Limited

(57) ABSTRACT

A fully convolutional network (FCN) implemented on a specialized processor optimized for convolution computation can achieve a speed-up in cell classification. Without re-optimizing the specialized processor, a further speed-up is achieved by compacting a testing image of cells, and processing the compacted testing image with the FCN. The testing image is first segmented into a background and regions of interest (ROIs). The ROIs are packed closer together by rearranging the ROIs without resizing them under a constraint that any two adjacent rearranged ROIs are separated by a distance in pixel not less than a minimum distance determined according to stride values of FCN convolutional layers. Geometrical operations in ROI rearrangement include relocating the ROIs and, optionally, rotating the ROIs. The rearranged ROIs are enclosed by a boundary, typically a rectangular boundary, to form the compacted testing image having an area smaller than that of the testing image.

25 Claims, 24 Drawing Sheets

(51) Int. Cl.
    *G16H 50/20*     (2018.01)
    *G06T 7/149*     (2017.01)
    *G06K 9/66*      (2006.01)
    *G06T 7/194*     (2017.01)
(58) Field of Classification Search
    USPC ........................................ 382/128, 164, 171
    See application file for complete search history.

(56) References Cited

U.S. PATENT DOCUMENTS

| | | | |
|---|---|---|---|
| 2017/0262735 A1 | 9/2017 | Ros Sanchez et al. | |
| 2018/0158189 A1* | 6/2018 | Yedla | G06T 7/11 |
| 2018/0253622 A1* | 9/2018 | Chen | G06N 3/0454 |

FOREIGN PATENT DOCUMENTS

| | | |
|---|---|---|
| CN | 107016681 A | 8/2017 |
| CN | 107256558 A | 10/2017 |
| CN | 107274386 A | 10/2017 |

OTHER PUBLICATIONS

Asli Kale, "Segmentation and classification of cervical cell images," M.Sc. Thesis, Bilkent University, Jan. 2010.
International Search Report and Written Opinion of PCT application No. PCT/CN2018/088765 issued from the International Search Authority dated Feb. 20, 2019.

* cited by examiner

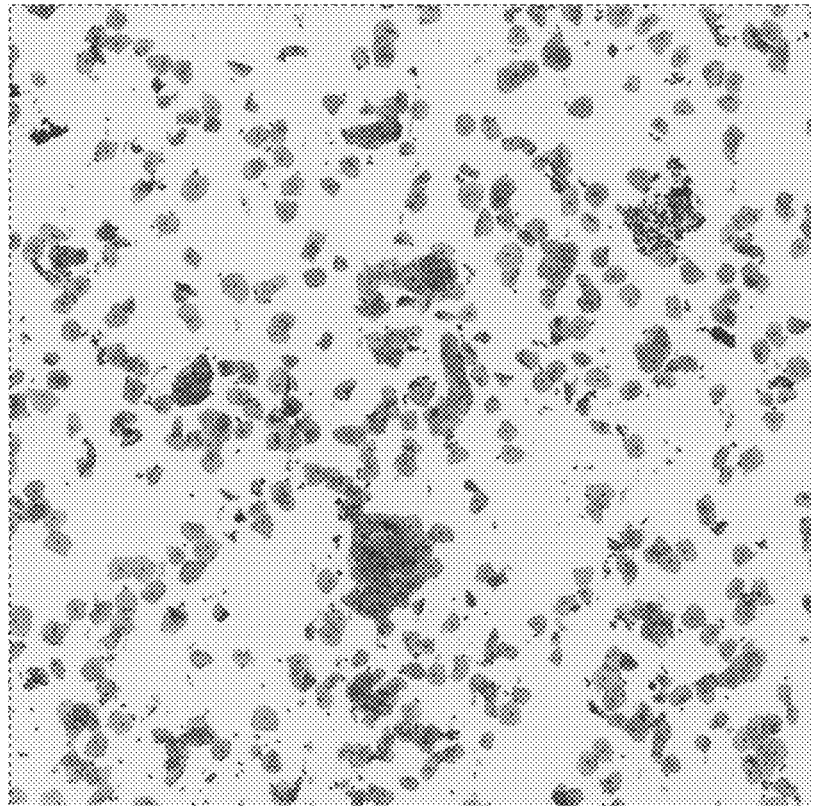
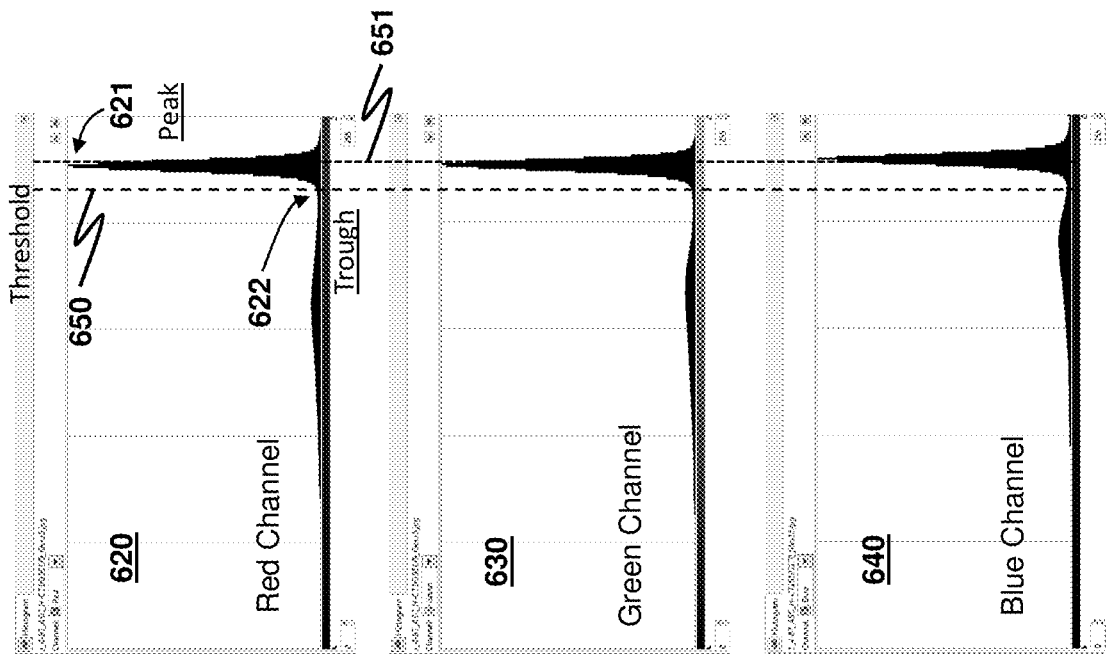
FIG. 6

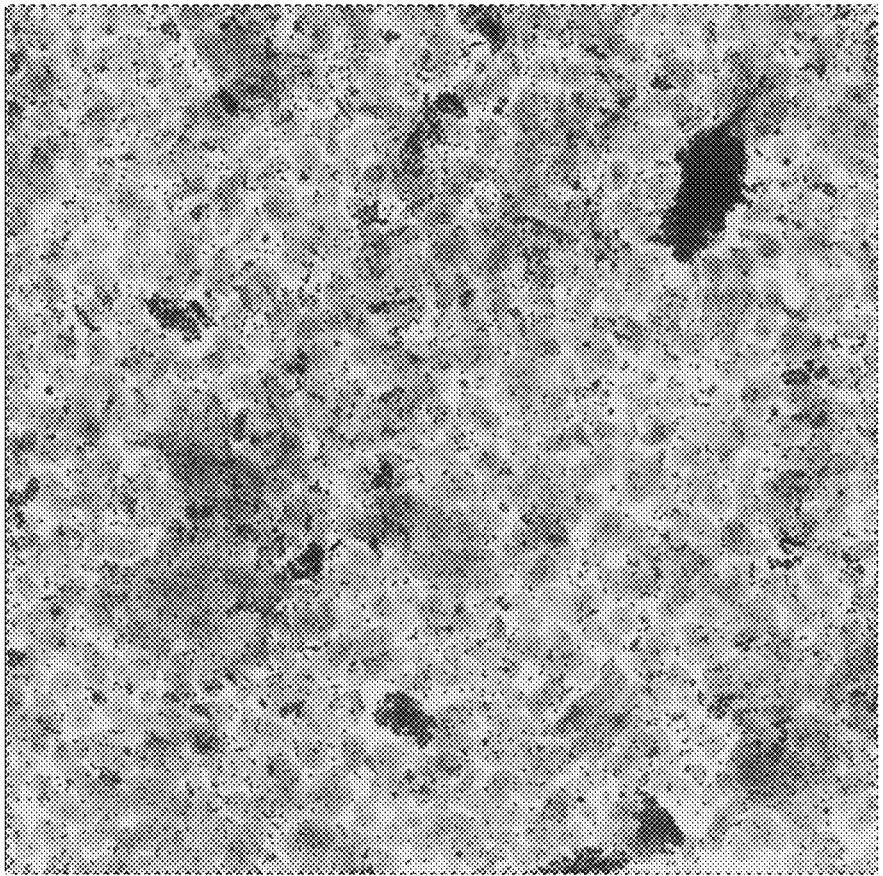
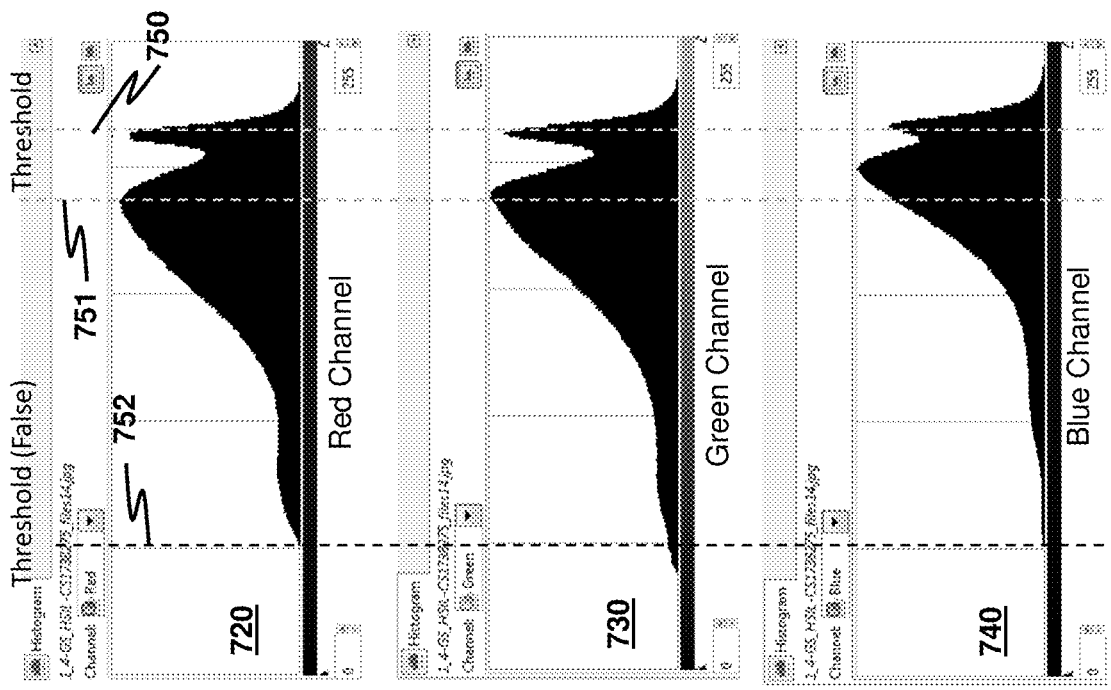
FIG. 7

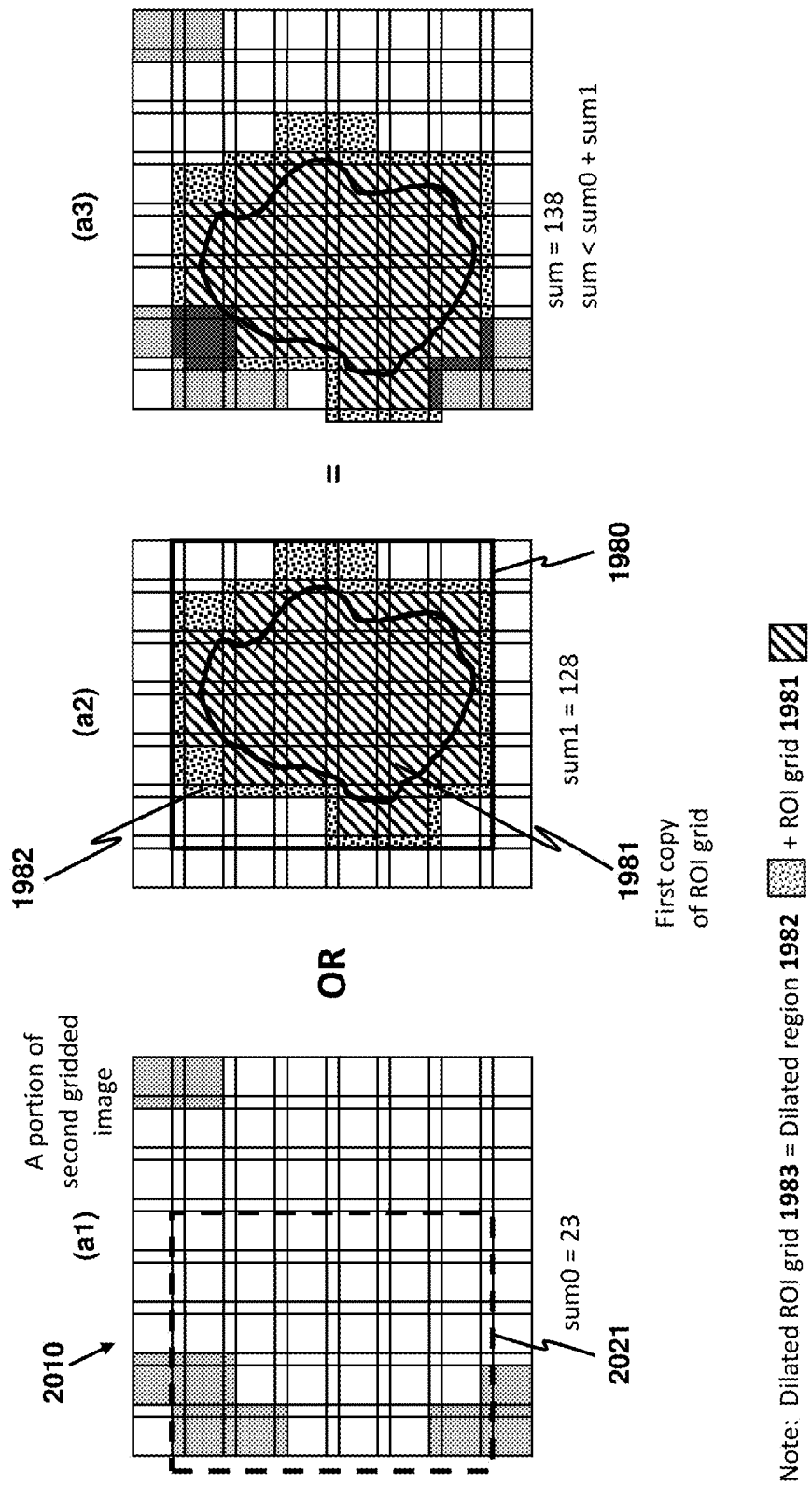

US 10,586,336 B2

IMAGE PRE-PROCESSING FOR ACCELERATING CYTOLOGICAL IMAGE CLASSIFICATION BY FULLY CONVOLUTIONAL NEURAL NETWORKS

LIST OF ABBREVIATIONS 2D two-dimensional
ADC adenocarcinoma endocervical
AGC atypical glandular cell
AIS adenocarcinoma in-situ
ASC-H atypical squamous cell-cannot exclude HSIL
ASC-US atypical squamous cell of undetermined significance
CNN convolutional neural network
FCN fully convolutional network
GPU graphics processing unit
HSIL high-grade squamous intraepithelial
LSIL low-grade squamous intraepithelial
RGB red, green, blue
ROI region of interest
SCC squamous cell carcinoma
TBS the Bethesda system
WSI whole slide image

FIELD OF THE INVENTION

The present invention relates to pre-processing a testing image for achieving a speed-up in cell classification performed by a FCN, where the FCN is implemented on a specialized processor optimized for convolution computation for images.

BACKGROUND

In automatic cancer screening, a sample containing cells taken from a human subject and transferred on a slide is imaged and the resultant cytological image is analyzed by a computer to search for any cancerous cell or precancerous abnormality. In the art, a CNN is often used to classify the cells for identifying possible cancerous cells or precancerous abnormalities due to the high classification accuracy achieved by the CNN, e.g., as used in a system disclosed in a pending U.S. patent application Ser. No. 15/910,131 filed Mar. 2, 2018, the disclosure of which is incorporated by reference herein. The CNN comprises plural layers for generating feature maps or heatmaps from a testing image. The last layer of the CNN is a classifying layer. Apart from the classifying layer, each of the remaining layers in the CNN may be a convolutional layer, a subsampling layer or a pooling layer. The classifying layer may be a fully connected layer or a convolutional layer. If the classifying layer is a convolutional layer, the CNN becomes a fully convolutional neural network or a FCN in short. Since computing a sequence of convolutional products for an image has a high degree of parallelism, specialized processors such as GPUs have been designed for exploiting this parallelism to speed up convolution computation for the image. The FCN can be implemented by a specialized processor with an optimized hardware configuration for speeding up cell classification. Advantageously, automatic cancer screening using the FCN for cell classification can be performed faster than using a CNN that employs a fully connected layer as a classifying layer. Despite a speed-up in cell classification is obtained by using the FCN, it is desirable if further speed-up can be achieved.

Usually, a typical testing image containing cells to be classified is sparse so that a large percentage of image area is often a background not contributory to cancer screening. However, the hardware configuration of the specialized processor is usually optimized to continuously compute convolutional products based on a sliding window-based scanning approach. A high percentage of computational effort may be wasted due to the sparsity of the cells in the testing image. A skipping methodology may be used, aiming at computing convolutional products for an identified plurality of ROIs each containing one or more cells clustered together while skipping convolution computation for the background. However, a significant drawback of using the skipping methodology is that jumping from one ROI to another in convolution computation destroys the inherent parallelism present in continuously computing convolutional products across an input image. The specialized processor, having an optimized hardware configuration for implementing the sliding-window scanning approach results in a low computation efficiency in executing the FCN for cell classification with the skipping methodology. Re-optimizing the hardware configuration to take into account the presence of skipping is very difficult if not impossible.

There is a need in the art for a technique to further speed up cell classification by using a FCN without a need to re-optimize the hardware configuration of the specialized processor.

SUMMARY OF THE INVENTION

A first aspect of the present invention is to provide a method for classifying a plurality of cells imaged on a testing image by using a FCN. The FCN has plural convolutional layers each having a respective value of stride. The FCN is implemented on a specialized processor having a hardware configuration optimized for computing plural convolutional products in parallel for an image.

The method comprises segmenting the testing image into a background and plural ROIs. An individual ROI comprises one or more connected individual cells disjoint from remaining cells in the plurality of cells.

The method further comprises compacting the testing image to form a compacted testing image. The compacting of the testing image includes rearranging the ROIs for packing the ROIs closer together under a first constraint that any adjacent two of the rearranged ROIs are separated in each of x- and y-directions of the testing image by a distance in pixel not less than a minimum distance determined according to the stride values of the convolutional layers. In particular, an individual ROI is rearranged by performing one or more geometric operations without resizing the individual ROI, where the one or more geometric operations include relocating the individual ROI. The forming of the compacted testing image includes enclosing an entirety of rearranged ROIs with a boundary. Typically, the boundary is a rectangular one. The boundary is a perimeter of the compacted testing image, and is selected under a second constraint that a first number of pixels occupied by the compacted testing image is less than a second number of pixels occupied by the testing image. The second constraint is equivalent to that the compacted testing image is smaller than the original testing image in area.

The method additionally comprises classifying the plurality of cells by processing the compacted testing image rather than the original testing image with the FCN. Advantageously, it results in a reduction of time required to accomplish the classifying of the plurality of cells without a need for re-optimizing the hardware configuration.

Preferably, the minimum distance is given by EQN. (1) to be detailed later.

Before the testing image is compacted, it is preferable to replace the background with a blank one in the testing image for minimizing interference due to the background in the classifying of the plurality of cells.

In the segmenting of the testing image into the background and the ROIs, a location and a contour of each of the ROIs on the testing image are also determined.

In one embodiment, the rearranging of the ROIs includes gridding the testing image with a grid unit to form a gridded image. The individual ROI is mosaicked to form a corresponding ROI grid on the gridded image. Thereby, plural ROI grids are formed on the gridded image. The grid unit is a rectangle having a width and a height each greater than or equal to the determined minimum distance. In one choice, the grid unit is a minimum grid unit, which is a square having a side length equal to the determined minimum distance. In another choice, the grid unit is a non-minimum grid unit. The rearranging of the ROIs further includes relocating the ROI grids on the gridded image one by one according to a descending order of ROI-grid size under a third constraint that the ROI grids after relocation do not overlap. In relocating the corresponding ROI grid on the gridded image with a directed displacement, the individual ROI on the testing image is also relocated with the same directed displacement.

According to one embodiment, the relocating of the ROI grids on the gridded image one by one according to the descending order of ROI-grid size under the third constraint comprises: creating a second gridded image having a dimension of the gridded image and being empty when created; copying the ROI grids one by one to the second gridded image according to the descending order of ROI-grid size; and relocating said corresponding ROI grid to the second location on the gridded image. The copying of said corresponding ROI grid to the second gridded image includes: dilating said corresponding ROI grid by one grid unit to form a dilated ROI grid; bounding the dilated ROI grid with a minimum bounding rectangle to form a rectangular window, wherein the rectangular window contains a first copy of said corresponding ROI grid; sliding the rectangular window on the second gridded image in a raster scanning manner along an x- or y-direction to identify a fitted region on the second gridded image such that in the fitted region, said first copy does not overlap with another ROI-grid copy already on the second gridded image; and putting said first copy on the fitted region, whereby a first location of said first copy on the second gridded image is same as a second location on the gridded image for said corresponding ROI grid to be relocated, thereby allowing the directed displacement to be determined.

Optionally, the one or more geometric operations used in rearranging the individual ROI further include rotating the individual ROI before relocation.

A first embodiment of the segmenting of the testing image into the background and the ROIs is applicable to the testing image that is a color one having plural color channels, each of the color channels having respective luminance data. The segmenting of the testing image includes: determining a threshold of luminance value for differentiating the ROIs from the background on the testing image; performing thresholding on each of the color channels according to the determined threshold to yield a respective binary image, whereby plural binary images for the color channels are obtained; performing a pixel-wise Boolean operation on the binary images to yield a mask, each pixel of the mask taking either a first value or a second value, the mask comprising islands of the first value, whereby an individual island on the mask corresponds to a respective ROI on the testing image, and a remaining part of the mask other than the islands corresponds to the background; filtering the mask for incorporating into the individual island any group of one or more pixels completely surrounded by the individual island and taken the second value; and determining a location and a contour of the individual island such that the determined location and contour of the individual island are a location and a contour of the respective ROI on the testing image.

In the first embodiment of the segmenting of the testing image, the determining of the threshold may comprise the steps of: (a) generating a respective histogram distribution of luminance data for each color channel, whereby plural histogram distributions for all the color channels are obtained; (b) for each color channel, identifying a first luminance value at which a highest peak in the respective histogram distribution occurs, and a second luminance value at which a trough immediately adjacent to the highest peak occurs, wherein the second luminance value is less than the first luminance value, whereby the second luminance values identified for the color channels are obtained; (c) determining whether a first condition is satisfied, wherein the first condition is that the second luminance values are greater than a limit predetermined for preventing occurrence of an overly-low threshold unsafe for being used in segmenting the testing image; (d) responsive to determining that the first condition is satisfied, setting the threshold according to a minimum one of the second luminance values; (e) responsive to determining that the first condition is not satisfied, performing the steps (f)-(h); (f) for each color channel, identifying a third luminance value at which a second highest peak in the respective histogram distribution occurs, whereby the third luminance values identified for the color channels are obtained; and (h) setting the threshold according to a minimum one of the third luminance values.

A second embodiment of the segmenting of the testing image into the background and the ROIs is applicable regardless of whether the testing image is a color one or a grayscale one. The segmenting of the testing image includes: creating a grayscale testing image having luminance data of the testing image; determining a threshold of luminance value for differentiating the ROIs from the background on the testing image, wherein the threshold is a mean value of luminance data of the grayscale testing image; performing thresholding on the grayscale testing image according to the determined threshold to yield a mask, each pixel of the mask taking either a first value or a second value, the mask comprising islands of the first value, whereby an individual island on the mask corresponds to a respective ROI on the testing image, and a remaining part of the mask other than the islands corresponds to the background; and determining a location and a contour of an individual island such that the determined location and contour of the individual island are a location and a contour of the respective ROI on the testing image.

A second aspect of the present invention is to provide a system that employs a FCN to classify plural cells into normal and abnormal cells according to any of the embodiments of the disclosed method.

The system comprises a first processor and a second processor.

The first processor is a specialized processor having a hardware configuration optimized for computing plural convolutional products in parallel for an image. The first processor is used for implementing the FCN. The FCN, having plural convolutional layers each having a respective value of stride, is used for classifying the plurality of cells.

The second processor is configured to execute a process for pre-processing the testing image before the plurality of cells is classified. The pre-processing process comprises the segmenting of the testing image into a background and plural ROIs, and the compacting of the testing image to form a compacted testing image, both according to any of the embodiments of the disclosed method. The pre-processing process further comprises sending the compacted testing image rather than the original testing image to the first processor for classifying the plurality of cells by the FCN, Thereby, a time required to accomplish the classifying of the plurality of cells is reduced without a need for re-optimizing the hardware configuration.

Other aspects of the present invention are disclosed as illustrated by the embodiments hereinafter.

BRIEF DESCRIPTION OF THE DRAWINGS

FIG. 6 depicts histogram distributions of luminance data in the color channels of the testing image for a general case that cells on the testing image are sparse.

FIG. 7 depicts histogram distributions of luminance data in the color channels of the testing image for a special case that cells on the testing image are densely packed.

DETAILED DESCRIPTION

Figure 1:
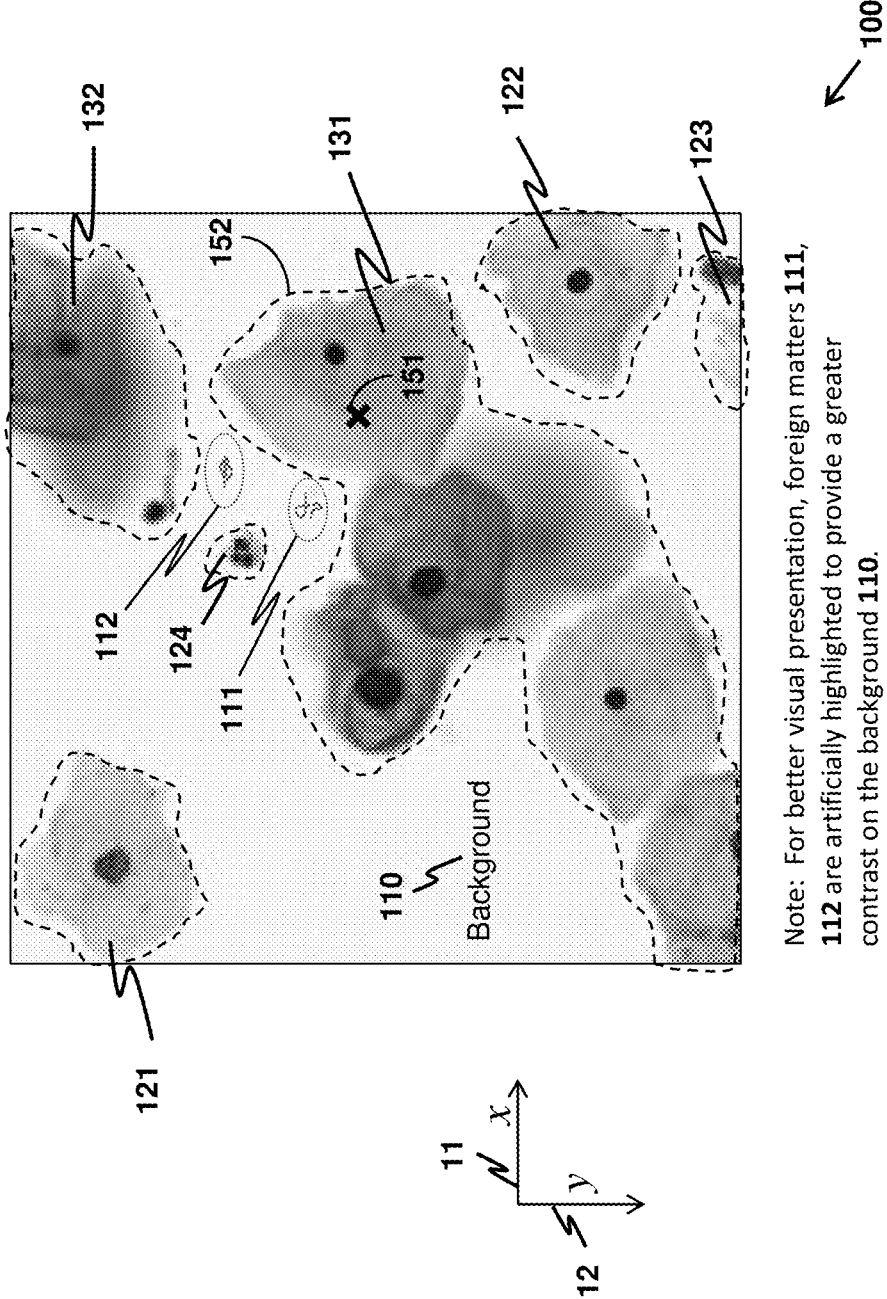
FIG. 1 depicts (a portion of) a typical real-life testing image.

As used herein, a testing image means an image processed, or intended to be processed, by a FCN for classification. Furthermore, herein in the specification and appended claims, it is understood that "an image containing a cell" means that the image contains a sub-image of the cell rather than that the image contains a physical cell.

In a convolutional layer of a FCN, a sequence of convolutional products generated for an input image, or a 2D array of data in general, is obtained by sliding a 2D filter on the input image and generating an individual sum of products each time when the filter stops at a position on the input image. "A stride" as commonly understood in the art is the number of pixels that the filter jumps from one position to an immediately next position. For example, the stride may have a value of 2 or less commonly a value of 3.

As will soon be shown, the testing image is usually a color image having plural color channels. Each color channel is individually processed by the FCN in convolution computation. After each color channel of the testing image is processed by plural convolutional layers in the FCN, outputs from the FCN for different color channels are visualized as one resultant color image, which is herein referred to as "a heatmap".

The present invention is concerned with pre-processing a testing image containing a plurality of cells where the pre-processed testing image is used by a FCN for classification of the cells. In particular, it is intended that the pre-processed testing image accelerates generation of classification results by the FCN when compared to processing the testing image without such pre-processing. Important applications of cell classification include cancer-cell screening and screening of precancerous abnormalities. However, the present invention is not limited to the applications of cancer-cell screening and precancerous-abnormality screening only. The present invention is usable for other medical and biological applications. Furthermore, it is not limited that the cells involved in the classification are originated from human beings only. The cells may be originated from animals such as horses, or from plants. Hereinafter, the present invention is exemplarily illustrated with reference to an application of the FCN classification for cervical cancer cell screening.

A testing image that is rectangular in shape has been a mainstream choice for FCN processing in cell classification. In preparing a sample of cells, however, it is possible that in some situations, using a non-rectangular container, such as a Petri dish, to hold the sample may be more preferred than using a rectangular slide. In these situations, it could be advantageous to use a testing image having a non-rectangular shape for cell classification where the sample is imaged to form the testing image. The present invention is applicable to a rectangular testing image as well as to a non-rectangular one. Since the rectangular testing image is still the mainstream choice for FCN processing, hereinafter the present invention is exemplarily illustrated by using a testing image that is rectangular in shape. Adapting the present invention for a non-rectangular testing image is provided wherever necessary.

In cancer-cell screening and precancerous-abnormality screening, cells to be classified are usually physically pre-processed in order to reveal certain specific structures present in the cells. In particular, in vitro staining is commonly used to color certain biological structures of interest in the cells, such as nuclei, to enhance contrast of such biological structures of interest with the structures' surroundings such that these structures are more easily located by a cytologist or a machine classifier such as a FCN. Hence, the testing image is usually a color image with a plurality of color channels, such as a set of red, blue and green color channels. Nevertheless, the present invention does not require that the testing image must be a color image. The testing image to be pre-processed by an application of the present invention may be a color image or a grayscale one.

Although real-life samples of the testing image used in the present disclosure for explaining the present invention are presented in grayscale images, the original samples are color images unless otherwise specified.

Before the present invention is detailed, it is insightful to first examine a typical testing image. FIG. 1 depicts (a portion of) a typical real-life testing image 100.

In the testing image 100, cells are standalone or are connected (or overlapped) together. A ROI is a region on the testing image 100 where there is a standalone cell or a cluster of connected cells, disjoint from remaining cells on the testing image 100. Attention of the cytologist or machine classifier is focused on the ROI, on which the one or more cells are examined to determine, for instance, if there is any cancerous cell or precancerous abnormality. On the testing image 100, ROIs 121-124 are standalone cells and ROIs 131, 132 are cell clusters. Each ROI is geometrically characterized with a location and a contour. Consider the ROI 131 as an example for illustration. The ROI 131 has a location 151 and a contour 152. Normally, the location 151 is selected to be a coordinate of a point inside the ROI 131. For example, the point may be conveniently selected to coincide with a nucleus of any cell in the ROI 131, or may be selected to be a center point of the ROI 131. The contour 152 is geometrically characterized by a set of coordinates referenced to the location 151. Those skilled in the art will appreciate that there are existing techniques for extracting the set of coordinates of the contour 152 from the testing image 100.

A background 110 is a remaining region on the testing image 100 where there is no ROI. Nevertheless, the background 110 is not necessarily an empty region. It may contain some foreign matters 111, 112 such as microorganisms not contributory to cancer-cell screening, or particulate contaminants. These foreign matters 111, 112 are likely to produce interference to cell classification. It is desirable if these foreign matters 111, 112 could be removed from the testing image 100 before cell classification is done.

Any image is a 2D image and has x- and y-directions. Herein in the present disclosure, a coordinate system having an x-direction 11 and a y-direction 12 is used whenever necessary in referencing an image. The x- and y-directions 11, 12 are mutually orthogonal.

Figure 2:
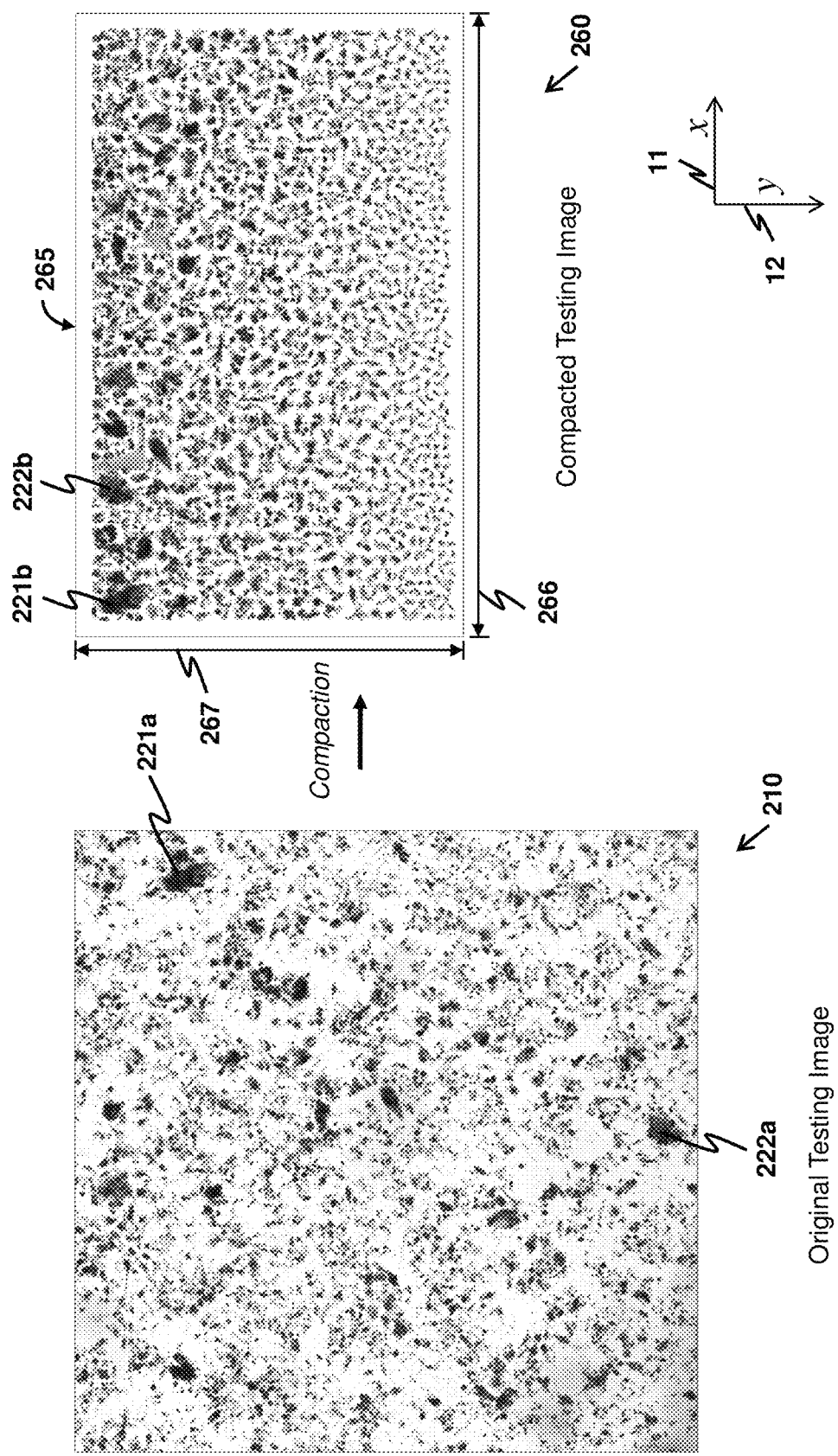
FIG. 2 provides a visualization of compacting an original testing image to form a compacted testing image to be used in FCN processing, for illustrating the main approach of obtaining a speed-up in cell classification.

The present invention aims at achieving a speed-up in cell classification by a FCN implemented on a specialized processor having a hardware configuration optimized for convolution computation for an image, where the speed-up is obtained without re-optimizing the hardware configuration. In particular, pre-processing a testing image before FCN processing is employed in the present invention. The main approach for achieving the speed-up is visualized in FIG. 2, which depicts compacting an original testing image 210 into a compacted testing image 260 to be used for FCN processing. On the original testing image 210, dark regions are ROIs containing information useful for cell classification whereas a brighter region is a background containing useless information not contributory to cell classification. By compacting the original testing image 210, useful information in the original testing image 210 is retained without loss while useless information is reduced, removed or minimized. The particular approach adopted in compacting the original testing image 210 is to pack the ROIs closer together, effectively reducing the background. In FIG. 2, packing the ROIs closer together is achieved by relocating ROIs. For example, ROIs 221a, 222a on the original testing image 210 are relocated to ROIs 221b, 222b on the compacted testing image 260, respectively. Note that the compacted testing image 260 has an area smaller than an area of the original testing image 210. Since the specialized processor is already optimized in hardware configuration for convolution computation for an image, it is not necessary to re-optimize the hardware configuration for FCN processing of the compacted testing image 260. Since the compacted testing image 260 is smaller in area than the original testing image 210, a direct reduction of the required computation time in cell classification is achieved without a need to re-optimize the hardware configuration of the specialized processor.

A. Disclosed Method

A first aspect of the present invention is to provide a method for classifying a plurality of cells imaged on a testing image by using a FCN. The FCN has plural convolutional layers each having a respective value of stride. Furthermore, the FCN is implemented on a specialized processor having a hardware configuration optimized for computing plural convolutional products in parallel for an image.

Figure 3:
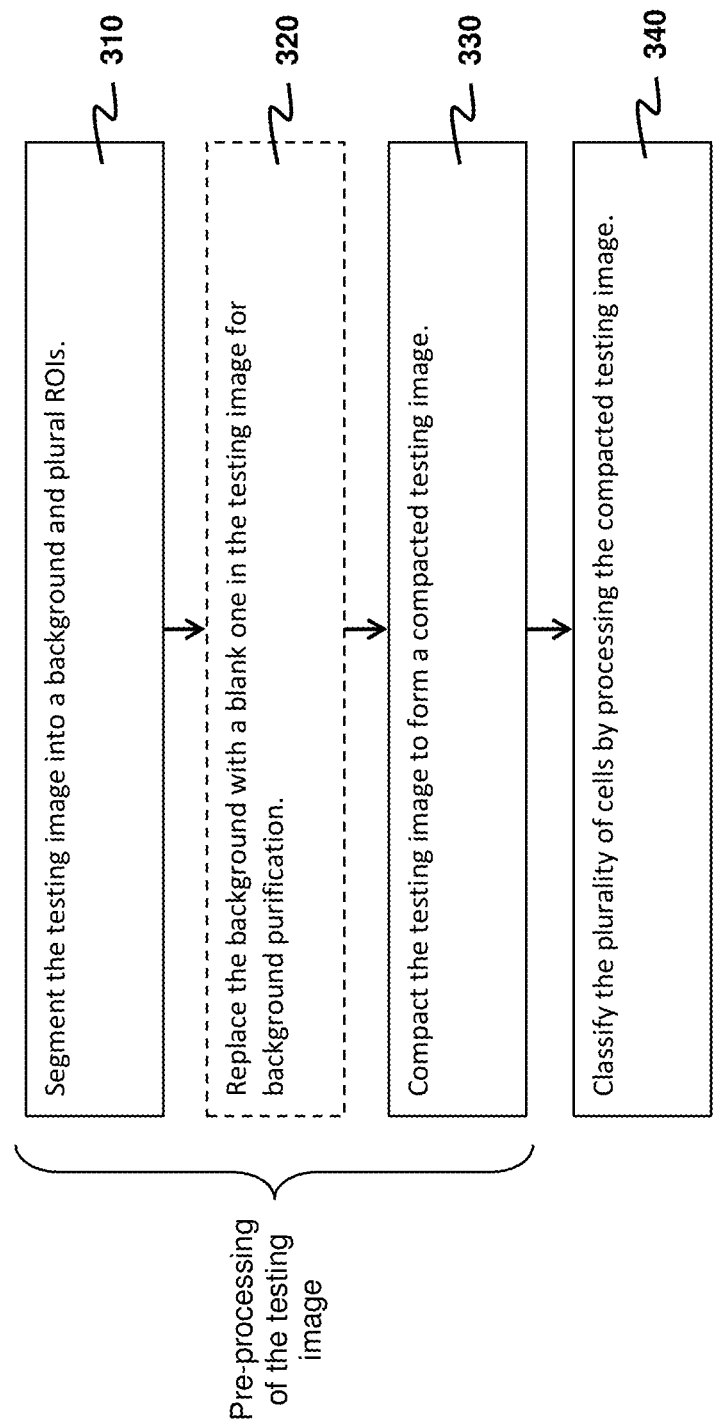
FIG. 3 depicts a flowchart of exemplary steps used in a method for classifying a plurality of cells with an advantage of speeding up cell classification.
Figure 4:
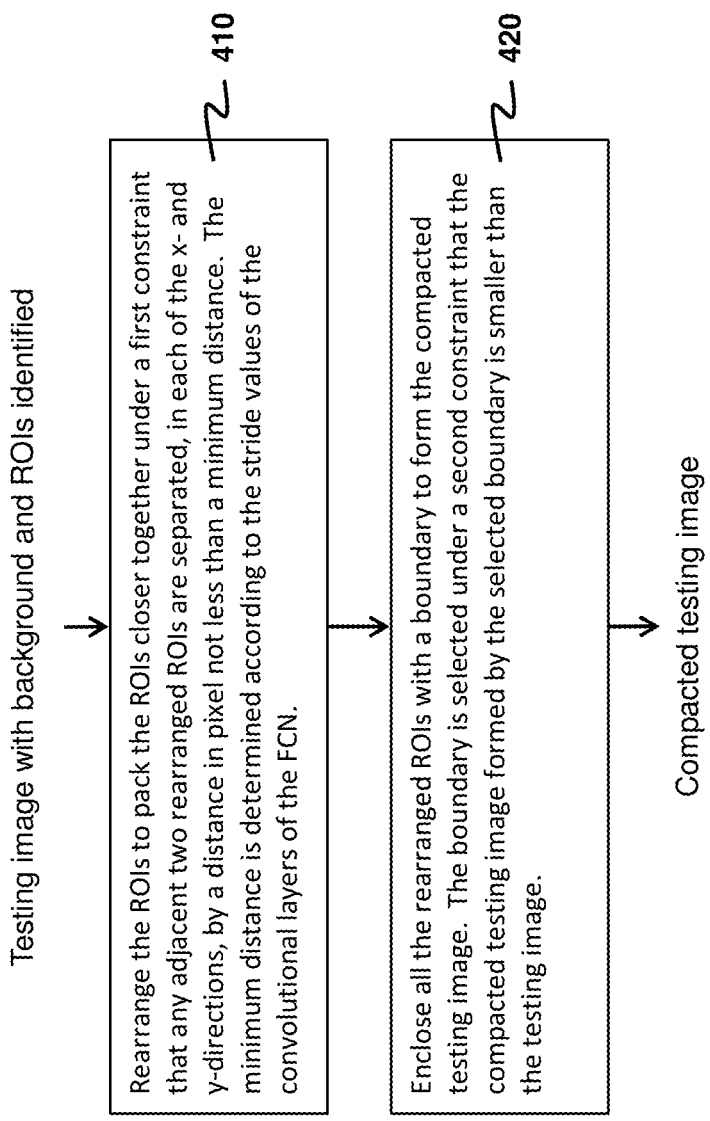
FIG. 4 depicts a flowchart for illustrating exemplary steps included in the step of compacting the testing image as disclosed in FIG. 3.

Exemplarily, the method is illustrated with the aid of FIGS. 3 and 4.

FIG. 3 depicts exemplary steps used in the disclosed method. In a step 310, the testing image is segmented into a background and plural ROIs. An individual ROI comprises one or more connected individual cells disjoint from remaining cells in the plurality of cells. As mentioned above, foreign matters in the background are likely to produce interference during cell classification. Since the background is identified in the step 310, it is preferable and advantageous to purify the background for minimizing interference due to the background during classifying the plurality of cells by the FCN. In a preferable step 320, purification is achieved by replacing the background with a blank one in the testing image. For example, each pixel belonging to the background in the testing image is set to have a value of 255 in each color channel of the pixel where the testing image is a 24-bit RGB image. In a subsequent step 330, the testing image is compacted to form a compacted testing image. Afterwards, the plurality of cells is classified in a step 340 by processing the compacted testing image rather than the original testing image with the FCN, thereby reducing a time required to accomplish classification of the plurality of cells without a need for re-optimizing the hardware configuration. Note that the steps 310, 320, 330 are used for pre-processing the testing image to generate the compacted testing image, which is subsequently processed by the FCN for cell classification.

FIG. 4 depicts a flowchart for illustrating exemplary steps included in the step 330 of compacting the testing image and forming the compacted testing image.

With the background and the ROIs identified and segmented, the ROIs are rearranged to pack the ROIs closer together, as in a step 410. Herein rearranging an individual ROI means performing one or more geometric operations without resizing the individual ROI. Furthermore, each geometric operation that is performed does not result in a loss of information carried by the individual ROI and necessary for cell classification. Relocating the individual ROI, as mentioned above in explaining FIG. 2, is one such geometric operation and is an essential operation in compacting the testing image. Another such geometric operation is rotating the individual ROI. It is less obvious that reflecting the individual ROI along a certain axis to invert the individual ROI is also one such geometric operation. (When a cell is put on a slide for classification by a cytologist, looking the cell from above the slide or from below does not change the type of cell it belongs to.)

Unlike rearrangement in other applications, cell classification using the FCN for a cytological image requires a clean site along cell edges; otherwise a rearranged cell (or a rearranged ROI) would have negative influence to its neighboring cells (or neighboring ROIs) during FCN processing. In the step 410, therefore, the rearranged ROIs are not only non-overlapped but also separated by at least a certain minimum distance in pixel in order to minimize or substantially reduce generation of inter-ROI interference during cell classification.

A preferred value of the minimum distance is determined based on the FCN configuration. Consider an example that a FCN has four layers each of which has a value of stride equal to 2. Under this FCN configuration, image data within a 16×16-pixel area on the testing image are condensed to form one pixel in a heatmap. Calculating from the center of the 16×16-pixel area on the testing image, one finds that pixels located on the testing image and separated from the center by more than 8 pixels do not contribute to the aforesaid one pixel in the heatmap. Hence, a minimum distance of 8 pixels is required to keep each rearranged ROI from interfering others in FCN processing. After generalization, the minimum distance, $d_{min}$, is calculated by $$d_{min} = \frac{1}{2} \Pi_{i=1}^{N} \varphi_i, \qquad (1)$$

where N is a total number of the convolutional layers in the FCN, and $\varphi_i$ is the stride value of ith convolutional layer.

In summary, the ROIs are rearranged under a first constraint that any adjacent two of the rearranged ROIs are separated in each of the x-direction 11 and the y-direction 12 of the testing image (see FIG. 2) by a distance in pixel not less than a minimum distance, where the minimum distance is determined according to the stride values of the convolutional layers of the FCN. Preferably, the minimum distance is calculated by EQN. (1).

After the ROIs are rearranged, an entirety of rearranged ROIs is enclosed with a boundary to form the compacted testing image in a step 420, where the boundary is a perimeter of the compacted testing image. The boundary may be rectangular or non-rectangular in shape. In a mainstream case that the FCN is intended to process rectangular images, the compacted testing image is rectangular in shape so that the boundary is a rectangular one. The boundary is selected under a second constraint that a first number of pixels occupied by the compacted testing image is less than a second number of pixels occupied by the testing image. The second constraint is equivalent to a requirement that the compacted testing image is smaller than the original testing image in area. Consider FIG. 2 for illustration. The compacted testing image 260 has a perimeter 265, which is a rectangular boundary (also denoted as 265) bounding all ROIs rearranged from the original testing image 210. The rectangular boundary 265 is selected such that the compacted testing image 260 has an area smaller than the original testing image 210's area.

In one option, the rectangular boundary 265 has a width 266 and a height 267 both measured in pixel, where each of the width 266 and the height 267 is selected to be minimally sufficient to enclose all the rearranged ROIs. In this choice, the rectangular boundary 265 becomes a minimum bounding rectangle. Nonetheless, it is possible that certain operational requirements may be imposed on the size of the compacted testing image 260. For example, the FCN may require that each of the width 266 and the height 267 be a power of two. In another option, each of the width 266 and the height 267 is selected to be minimally sufficient to enclose all the rearranged ROIs while satisfying one or more image-size requirements of the FCN in processing the compacted testing image 260.

Further aspects of the disclosed method are elaborated as follows.

A.1. Segmenting the Testing Image (Step 310): First Embodiment

Figure 5:
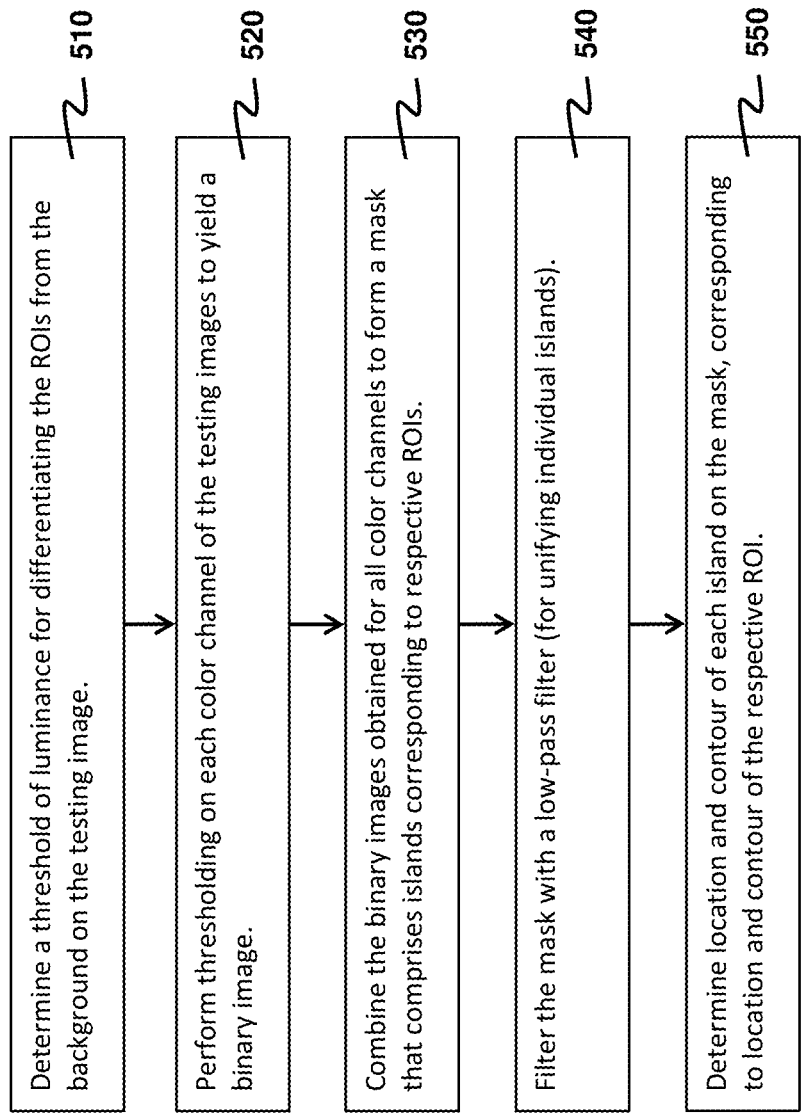
FIG. 5 provides a flowchart having exemplary processing steps included in a first embodiment of the step of segmenting the testing image into the background and the ROIs as disclosed in FIG. 3, where the testing image is a color one having plural color channels.

FIG. 5 is a flowchart showing exemplary processing steps included in the step 310 according to a first embodiment thereof. The first embodiment of the step 310 is applicable to the testing image that is a color one having plural color channels. Each of the color channels has respective luminance data.

A.1.1. Determining a Threshold for Image Segmentation (Step 510)

In a step 510, a threshold of luminance value for differentiating the ROIs from the background on the testing image is determined. The step 510 is illustrated as follows with the aid of FIGS. 6-8.

Figure 8:
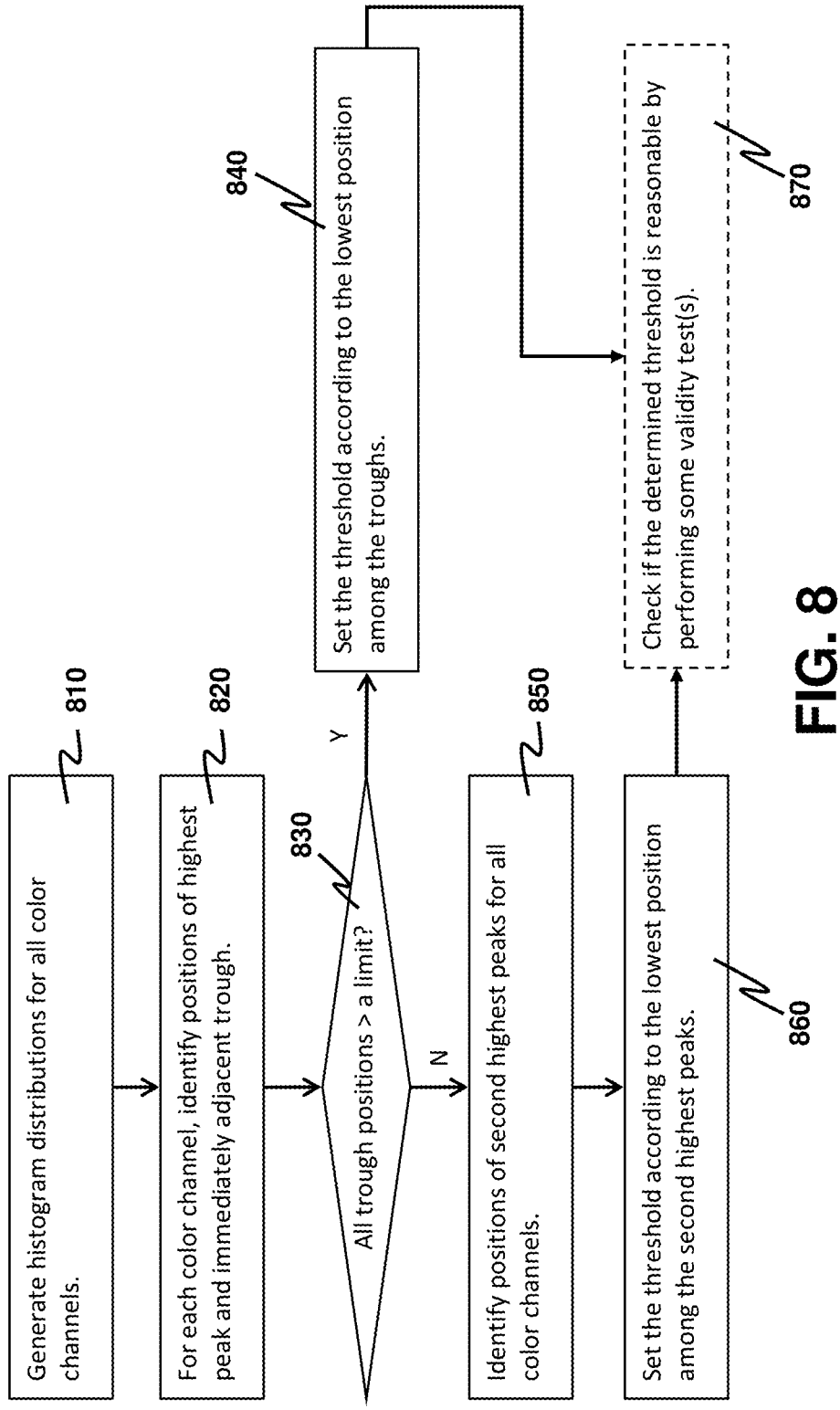
FIG. 8 depicts a flowchart showing exemplary processing steps included in the step of determining the threshold for differentiating the ROIs from the background on the testing image, where the processing steps are based on the observations of FIGS. 7 and 8.

FIG. 8 depicts a flowchart showing exemplary processing steps included in the step 510 of determining the threshold of luminance value for differentiating the ROIs from the background on the testing image. Explanation of these processing steps are facilitated by considering a general case and a special case of the testing image as depicted in FIGS. 6 and 7, respectively.

In the general case shown in FIG. 6, a typical testing image 610, being a color image, has three histogram distributions 620, 630, 640 for red, green and blue color channels, respectively. The x-axis of each of the distributions 620, 630, 640 is a luminance value ranging from 0 to 255, where a value of 255 means that a highest degree of luminance is achieved. The testing image 610 is typical in that cells thereon are sparse and well dispersed over the testing image 610. As a result of the background dominating the testing image 610, in each of the three histogram distributions 620, 630, 640, there is consistently a highest peak 621 appeared at roughly around a first x-axis position 651. It is possible to identify a trough 622 (i.e. a local minimum) immediately adjacent to the highest peak 621 where the trough 622 has a second x-axis position 650 on the left of the first x-axis position 651. That is, a luminance value corresponding to the second x-axis position 650 is less than that of the first x-axis position 651. Therefore, it is instructive to set the threshold for segmenting the backgrounds from ROIs on the testing image 610 as the luminance value corresponding to the second x-axis position 650.

In the special case shown in FIG. 7, another testing image 710 is decomposed into red, green and blue color channels having respective histogram distributions 720, 730, 740, where the x-axis of each of the distributions 720, 730, 740 is a luminance value ranging from 0 to 255. This testing image 710 is denser in cell packing than the typical testing image 610. A highest peak in each of the three histogram distributions 720, 730, 740 roughly appears at a first x-axis position 751 (although the histogram distribution 740 of the blue color channel has a highest peak somewhat off from the first x-axis position 751). In each of the three histogram distributions 720, 730, 740, a trough immediately adjacent to the highest peak and on the left of the first x-axis position 751 is estimated to have a second x-axis position 752. Clearly, the second x-axis position 752 has a very low luminance value. It follows that in performing the step 310 to segment the testing image 710, an unreasonable high percentage of the testing image 710 would be identified as the background, so that portions of the cells on the testing image 710 would be masked out. As a fail-safe measure, a second highest peak is searched over the histogram distributions 720, 730, 740, and is assigned as the threshold for image segmentation. The second highest peak is estimated to have a third x-axis position 750.

Based on the observations for the two cases of FIGS. 6 and 7, the procedure of determining the threshold for the first embodiment of the step 510 is depicted in FIG. 8.

In a step 810, a respective histogram distribution of luminance data is generated for each color channel. Thereby, plural histogram distributions for all the color channels are obtained.

In a step 820, identify for each color channel: 1) a first luminance value at which a highest peak in the respective histogram distribution occurs; and 2) a second luminance value at which a trough immediately adjacent to the highest peak occurs. Particularly, the second luminance value is less than the first luminance value. As a result of the step 820, the second luminance values identified for the color channels are obtained.

After the second luminance values are obtained, whether a first condition is satisfied is determined in a step 830. The first condition is that the second luminance values are greater than a limit predetermined for preventing occurrence of an overly-low threshold unsafe for being used in segmenting the testing image. Although an advantageous value of the limit varies from one testing image to another, the Inventors have found from experiments that in general, the limit may be advantageously set to be about two-third of a maximum luminance value used in the histogram distributions. For example, the maximum luminance value is 255 for the two cases of FIGS. 6 and 7, so that the limit is conveniently set to be 170.

If the first condition is satisfied, then set the threshold according to a minimum one of the second luminance values (step 840). In one choice, the threshold is set as the minimum second luminance value. Anyway, it is sometimes advantageous to increase or decrease the threshold with some offset from the minimum second luminance value. In a conservative choice for retaining more information of the cells on the testing image, the threshold is increased by adding a positive offset to the minimum second luminance value. In another approach that aims at more reduction on the FCN computation time, the threshold is made lower than the minimum second luminance value in order to reduce a total area occupied by the ROIs at the expense of some loss in cell information.

If the first condition is not satisfied, identify a third luminance value at which a second highest peak in the respective histogram distribution occurs (step 850), so that the third luminance values identified for the color channels are obtained. The threshold is then set according to a minimum one of the third luminance values (step 860). Similar to the step 840, the threshold may be set as the minimum third luminance value, or may be increased or decreased from the minimum third luminance value by a certain offset.

After the threshold is determined in the step 840 or the step 860, the determined threshold may be checked with one or more validity tests to analyze if the determined threshold is reasonable or not (step 870). One example is given as follows. After a plurality of cells is deposited on a slide and is performed with certain in vitro staining, it is desirable to reveal colors of the cells as faithfully as possible. It is done by illuminating the slide with a spectrally white light source. The illuminated slide is then imaged to form a testing image. Hence, the background of the testing image is predominantly white. A white color is formed by mixing red, green and blue colors in roughly the same amount. In case the threshold is obtained from the step 840, the first luminance values identified in the step 820 for the color channels are checked to determine if the difference between the maximum and minimum of the first luminance values is within a certain acceptable limit that ensures whiteness of the background. In case the threshold is obtained from the step 860, the third luminance values obtained in the step 850 are similarly checked. In case the determined threshold does not pass the one or more validity tests in the step 870, another approach of segmenting the testing image is required for accomplishing the step 310. Such another approach will be elaborated later.

A.1.2. Thresholding and Combining to Form a Mask (Steps 520, 530)

Refer to FIG. 5. According to the determined threshold, thresholding on each of the color channels is performed in a step 520. By thresholding a color channel, it is meant that the luminance value of each pixel on the color channel is compared with the determined threshold to yield a single yes-no result that indicates whether the pixel under thresholding is greater (less) than, or is not greater (less) than, the threshold. Hence, a binary image is generated. Each pixel of the binary image takes either a first value or a second value. Most often the first and second values are Boolean values selected from 0 and 1 in computer implementation of the step 520. As a result of thresholding on all the color channels, plural binary images for the color channels are obtained in the step 520.

Figure 9:
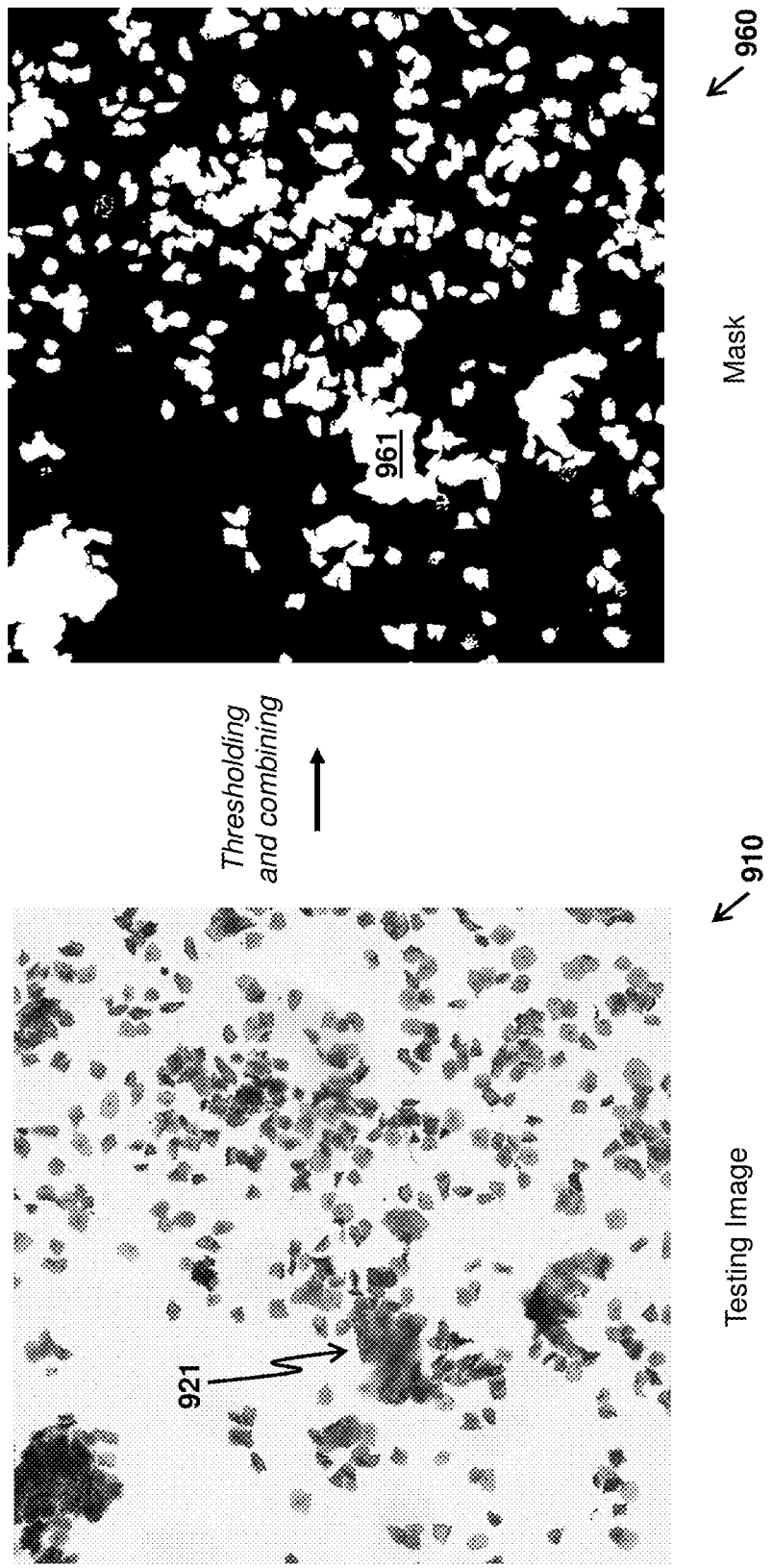
FIG. 9 provides an illustrative example of thresholding the testing image and combining resultant binary images to form a mask for separating the background from the ROIs in the testing image.

In a step 530, the binary images for the color channels are combined to yield a mask by performing a pixel-wise Boolean operation on the binary images. FIG. 9 provides an illustrative example of thresholding color channels of a testing image 910 and combining resultant binary images to form a mask 960. The mask 960 is a black-and-white image. It is noted that the mask 960 contains plural islands in a white color. In particular, a ROI 921 on the testing image 910 has a corresponding island 961 on the mask 960. As such, an individual island on the mask 960 corresponds to a respective ROI on the testing image 910, and a remaining part of the mask 960 other than the islands corresponds to the background.

In selecting the Boolean operation in combining the binary images to form the mask, there are different choices. For example, one may select the Boolean operation such that when the binary images are viewed as respective primary-color images (e.g., of red, green and blue colors) and collectively form a color image, a non-white pixel is treated as a dark pixel in the mask 960. In another example, a conservative approach for retaining more information of the cells on the testing image is adopted. The Boolean operation is selected such that an entirety of the islands on the mask 960 is a union of all islands on the binary images. Yet in another approach that aims at more reduction on the FCN computation time, the reverse to the aforementioned conservative approach is adopted in order to reduce a total area occupied by the islands on the mask 960 at the expense of some loss in cell information.

For convenience in illustrating the present invention, hereinafter it is assumed that a white color and a black color taken by a pixel in the mask 960 correspond to taking the first value and the second value by the pixel, respectively. Hence, a pixel in an individual island of the mask 960 has the first value.

A.1.3. Filtering the Mask (Step 540)

Figure 10:
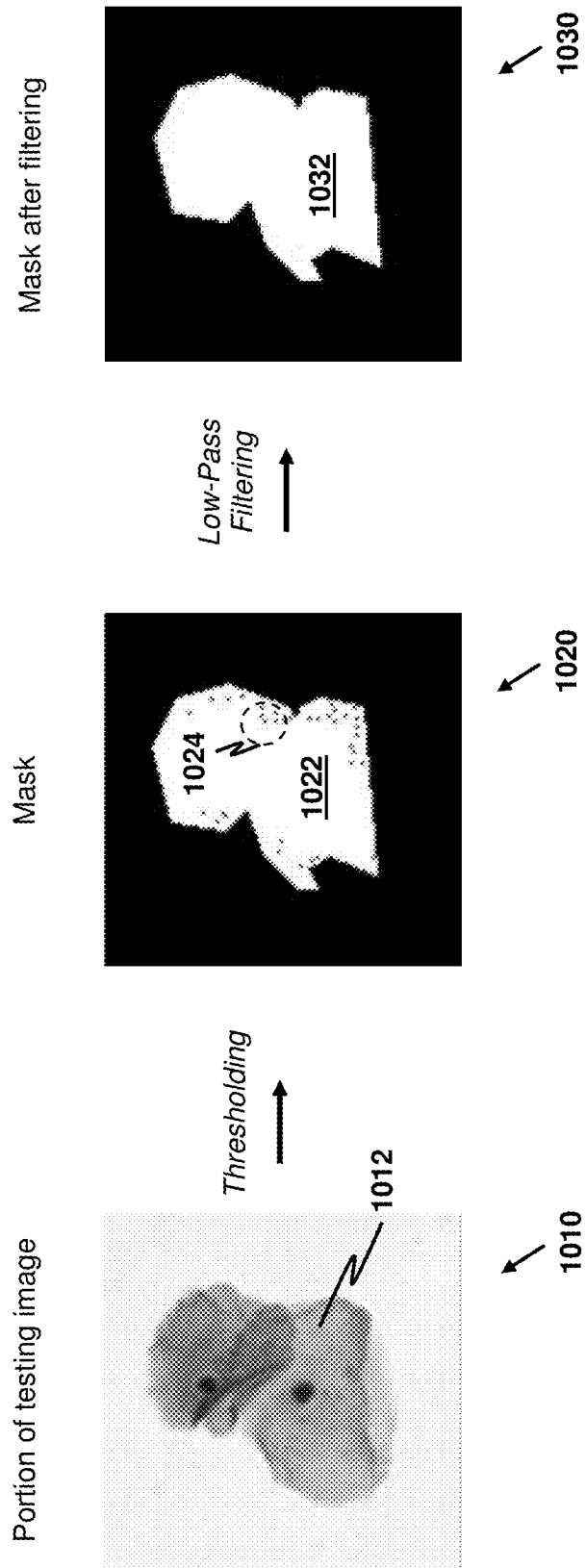
FIG. 10 illustrates unification of an individual island on the mask by low-pass filtering the mask.

Color histogram thresholding in the step 520 takes a very short time. Despite this advantage, some pixels inside the islands on the mask 960 would be incorrectly taken as the background. FIG. 10 illustrates this phenomenon and explains a need for low-pass filtering. A sample testing image 1010, being a color image, is performed with thresholding and then a mask 1020 is formed. The sample testing image 1010 has a ROI 1012 therein. On the mask 1020, an island 1022 corresponds to the ROI 1012. The island 1022, taking the first value, is contaminated with plural pixel clusters 1024, where each of the pixel clusters 1024 has one or more pixels taken the second value (indicating that the one or more pixels correspond to the background).

The presence of the pixel clusters 1024 in the island 1022 may be acceptable in usual image-processing applications. However, in cervical-cancer diagnosis, it could be fatal. To remove the pixel clusters 1024, the mask 1020 is filtered in a step 540 with a low-pass filter for incorporating into the island 1022 any group of one or more pixels completely surrounded by the island 1022 and taken the second value (that is, the pixel clusters 1024). A filtered mask 1030 is obtained. One choice of the low-pass filter is a median filter. After filtering, the island 1022 (shown as island 1032) becomes a contiguous one.

A.1.4. Determining the Location and Contour of the Individual Island (Step 550)

As mentioned above in illustrating FIG. 1, the ROI 131 is geometrically characterized by determining the location 151 and the contour 152 of the ROI 131. In a step 550, determine a location and a contour of the individual island on the mask after low-pass filtering is performed in the step 540. The determined location and contour of the individual island are respectively a location and a contour of the respective ROI on the testing image corresponding to the individual island on the mask.

A.2. Segmenting the Testing Image (Step 310): Second Embodiment

Figure 11:
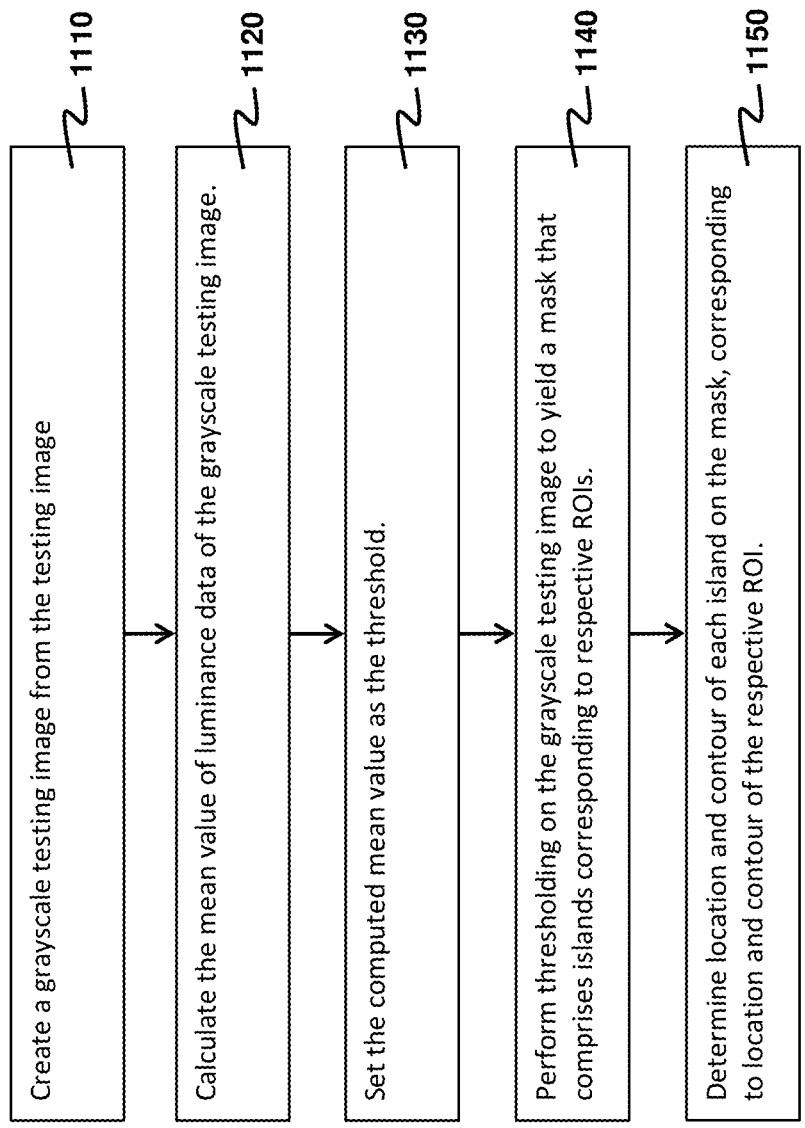
FIG. 11 provides a flowchart having exemplary processing steps included in a second embodiment of the step of segmenting the testing image into the background and the ROIs as disclosed in FIG. 3.

FIG. 11 depicts a flowchart showing exemplary processing steps included in the step 310 according to a second embodiment thereof. Different from the first embodiment of the step 310 as disclosed above, the second embodiment is applicable regardless of whether the testing image is a color one or a grayscale one.

In determining the background from the ROIs, a grayscale version of the testing image is required, which is referred to as a grayscale testing image. If the testing image is already a grayscale one, the grayscale testing image is immediately obtained. If the testing image is a color one, techniques for converting the testing image to the grayscale one are available in the art. In a step 1110, a grayscale testing image having luminance data of the testing image is created.

A mean value of luminance data of the grayscale testing image is computed in a step 1120. In a step 1130, the computed mean value is set as the threshold.

After the threshold is determined, thresholding on the grayscale testing image according to the determined threshold is performed in a step 1140 to yield a mask. Each pixel of the mask takes either a first value or a second value. The mask comprises islands of the first value. Similar to the explanation given to the steps 520 and 530 above, an individual island on the mask corresponds to a respective ROI on the testing image, and a remaining part of the mask other than the islands corresponds to the background.

In a step 1150, a location and a contour of an individual island is determined such that the determined location and contour of the individual island are a location and a contour of the respective ROI on the testing image. The step 1150 is essentially the same as the step 550 elaborated above.

A.3. Rearranging the ROIs to Pack the ROIs Closer Together (Step 410)

Figure 12:
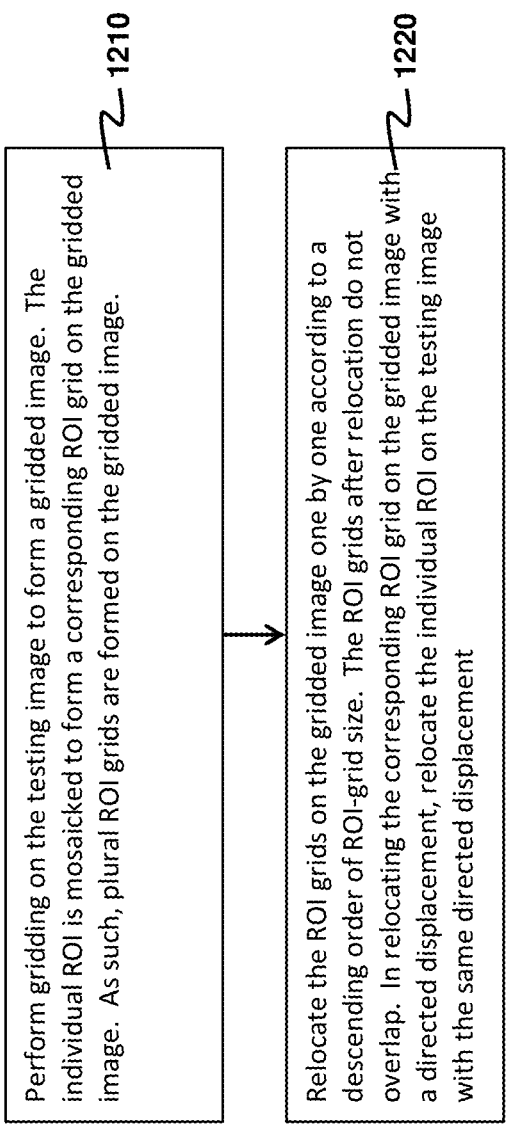
FIG. 12 provides a flowchart showing, in accordance with one embodiment of the present invention, processing steps included in the step of rearranging the ROIs.

FIG. 12 is a flowchart showing, in accordance with one embodiment of the present invention, processing steps included in the step 410 of rearranging the ROIs for packing the ROIs closer together under the above-mentioned first constraint that any two adjacent rearranged ROIs are separated in each of the x- and y-directions by at least the determined minimum distance. The step 410 is explained as follows with the aid of FIGS. 13 and 14. The rearrangement of the ROIs is performed after the location and contour of each ROI are obtained.

Figure 13:
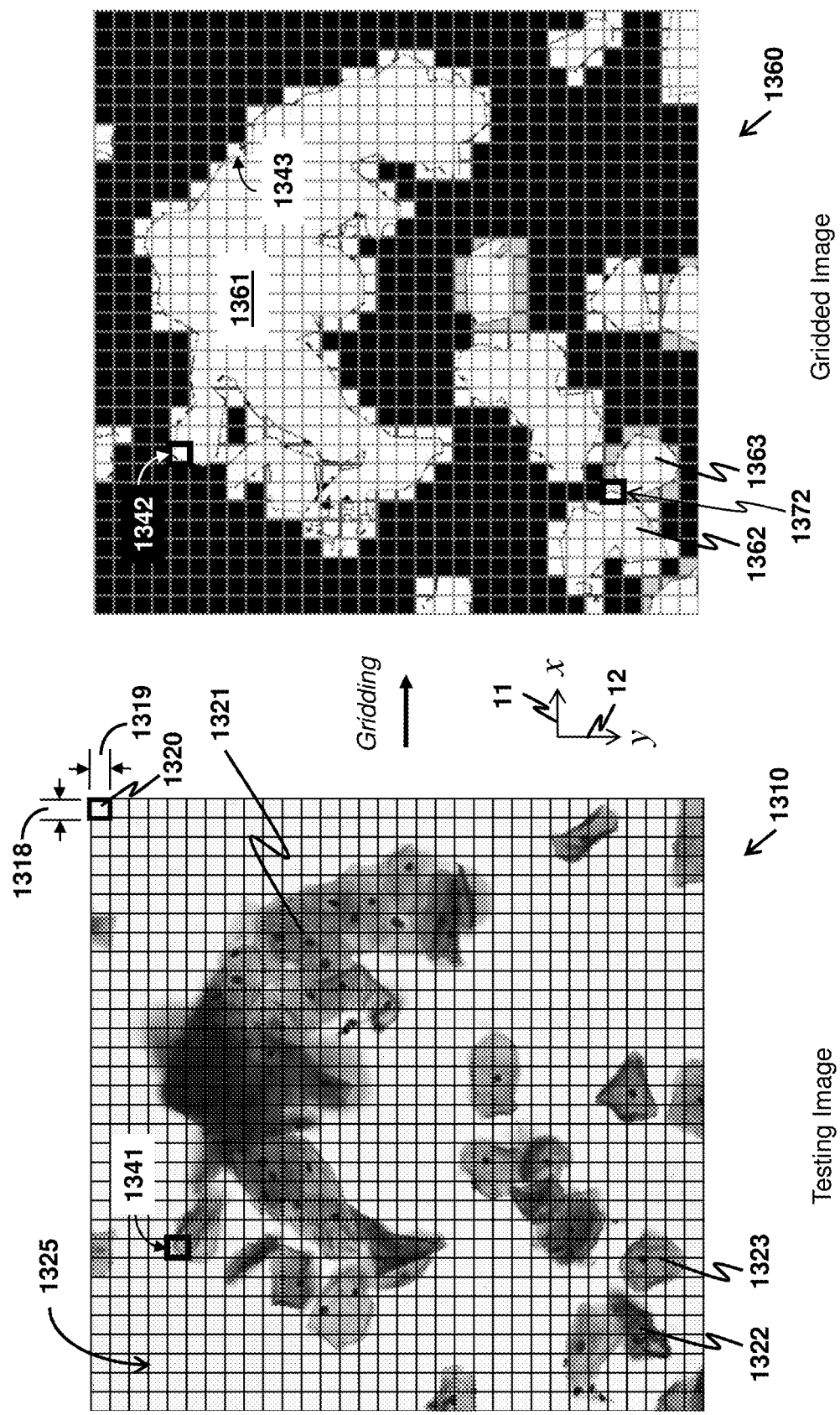
FIG. 13 depicts an example of gridding the testing image to form a gridded image.

In a step 1210, the testing image is gridded to form a gridded image. For explaining the step 1210, FIG. 13 depicts an example of gridding a testing image 1310 having plural ROIs to form a gridded image 1360. A grid 1325 is first superimposed on the testing image 1310, where the grid 1325 divides the testing image 1310 into a plurality of rectangles. In a general setting, the rectangles are not necessarily of the same size but are required to collectively fill up the testing images 1310 without any void. Conveniently, the grid 1325 for dividing the testing image 1310 is formed by repeating a grid unit 1320 along both the x- and y-directions 11, 12, where the grid unit 1320, being a rectangle, has a width 1318 and a height 1319 each greater than or equal to the minimum distance determined in the step 410. In one preferable choice, the grid unit 1320 is a square whose width 1318 and height 1319 each have a length of the minimum distance. Each of the ROIs is mosaicked to form a corresponding ROI grid. For example, ROIs 1321-1323 are mosaicked to form ROI grids 1361-1363, respectively. By mosaicking an individual ROI to form a corresponding ROI grid, it is meant that if a pixel belonging to the individual ROI on the testing image 1310 resides in a particular square in the grid 1325, the corresponding ROI grid on the gridded image 1360 also includes this particular square. Take the ROI 1321 as an example. The ROI 1321 has plural pixels on a square 1341 of the grid 1325, and hence the ROI grid 1361 includes a corresponding square 1342. Note that the contour of the ROI 1321 (shown as contour 1343) is required in determining the ROI grid 1361. It is also possible that multiple ROI grids overlap in the gridded image 1360. For example, although the ROIs 1322, 1323 are disjoint on the testing image 1310, their respective ROI grids 1362, 1363 overlap on a square 1372.

Figure 14:
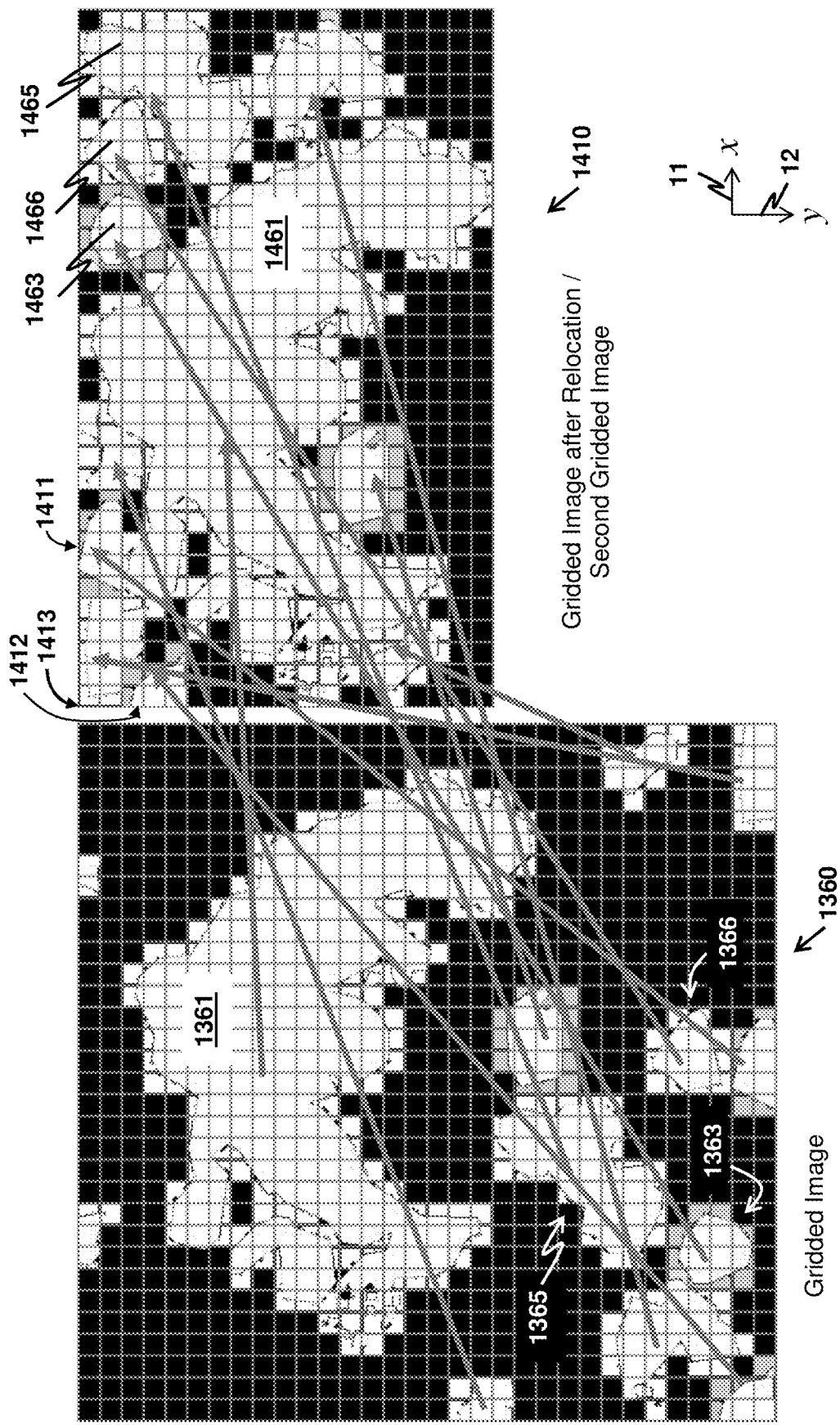
FIG. 14 depicts relocating the ROI grids on the gridded image of FIG. 13 without overlapping.

After the gridded image 1360 is obtained, the ROI grids thereon are relocated, in a step 1220, one by one according to a descending order of ROI-grid size under a third constraint that the ROI grids after relocation do not overlap. FIG. 14 depicts relocating the ROI grids on the gridded image 1360 according to the step 1220. Among the ROI grids on the gridded image 1360, the (first) ROI grid 1361 is the largest one. It is relocated on a second gridded image 1410 as a first relocated ROI grid 1461. The second gridded image 1410 may also be regarded as the gridded image 1360 after relocation. The second gridded image 1410 has a top side 1411 and a left side 1412 joined at a top-left corner 1413. Note that the first relocated ROI grid 1461 is positioned close to the top side 1411 and the left side 1412 to minimize a possible space around the top-left corner 1413 and not occupied by the first relocated ROI grid 1461. This possible space would waste FCN processing time in cell classification if not further used up by other relocated ROI grid(s). The next largest ROI grid on the gridded image 1360 is a second ROI grid 1365, which is relocated as a second relocated ROI grid 1465. In particular, the second relocated ROI grid 1465 is positioned close to the top side 1411 and the first relocated ROI grid 1461 also for minimizing a possible space that would otherwise waste FCN processing time. In the example of FIG. 14, the space between the first and second relocated ROI grids is filled up by smaller relocated ROI grids 1463, 1466 respectively originated from ROI grids 1363, 1366 on the gridded image 1360.

In general, each ROI grid on the gridded image 1360 is usually relocated at a first available place searched from the top-left corner 1413. However, ROI grids smaller than the largest one (the first ROI grid 1361) may be processed based on a randomly selected starting position on the second gridded image 1410 in order to avoid concentrating ROIs at a certain location. In addition, the width 1318 and the height 1319 of the grid unit 1320 may be individually varied in order to pack the ROI grids as densely as possible.

Consider that the second gridded image 1410 is the same as the gridded image 1360 except that the ROIs on the gridded image 1360 are relocated. Also consider moving the first ROI grid 1361 as an illustrative example. The location of the first ROI grid 1361 is known as a result that the corresponding ROI 1321 on the testing image 1310 is known. Since the location of the first ROI grid 1361 on the gridded image 1360 after relocation is known, a directed displacement (i.e. a distance with a direction) of moving the first ROI grid 1361 to become the first relocated ROI grid 1461 can be computed in the step 1220. This directed displacement is usable as the same directed displacement of relocating the ROI 1321 on the testing image 1310 in the rearrangement of ROIs for compacting a testing image into a compacted testing image.

A.4. Gridded Image with a Minimum Grid Unit

In the special case that the grid unit 1320 has both the width 1318 and the height 1319 equal to the minimum distance that is determined in the step 410, the grid unit 1320 is herein referred to as a minimum grid unit. The minimum grid unit is a square.

A.4.1. Relocating the ROI Grids on the Gridded Image (Step 1220)

Figure 15:
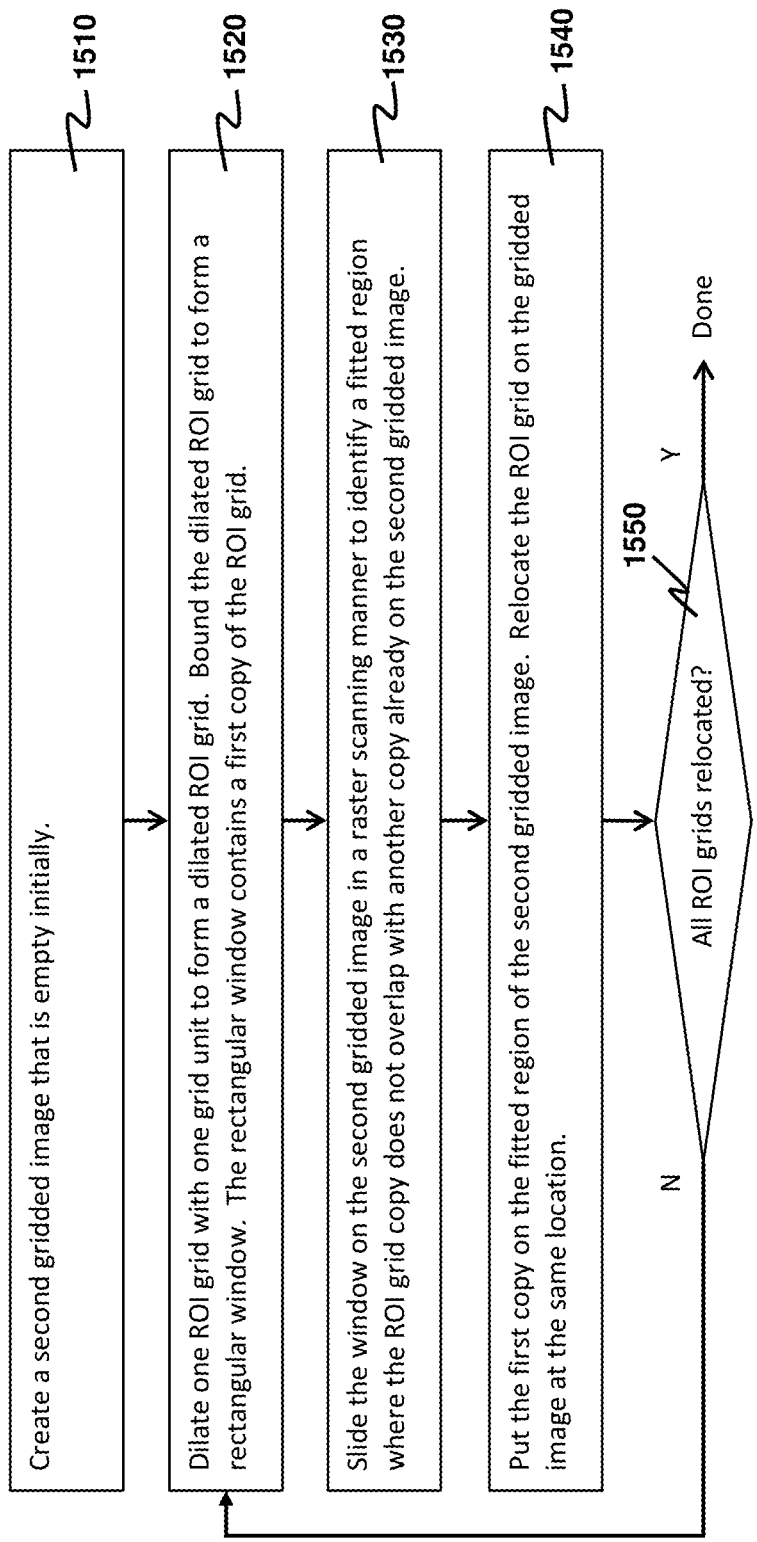
FIG. 15 provides a flowchart showing, in accordance with one embodiment of the present invention, processing steps of relocating the ROI grids on the gridded image when the gridded image has a minimum grid unit, namely, a square having a side length of minimum distance.

FIG. 15 is a flowchart showing, in accordance with one embodiment of the present invention, processing steps included in the step 1220 of relocating the ROI grids on the gridded image 1360 when the grid unit 1320 is selected to be a minimum grid unit. The ROI grids are relocated one by one according to the descending order of ROI-grid size under the above-mentioned third constraint that the ROI grids after relocation do not overlap.

In a step 1510, create the second gridded image 1410 that is empty when created. The second gridded image 1410 is a temporary space used for determining the directed displacement of an individual ROI grid under the third constraint. Thus, the second gridded image 1410 when created has a dimension of the gridded image 1360.

Steps 1520, 1530, 1540 and 1550 are used for copying the ROI grids on the gridded image 1360 one by one to the second gridded image 1410 according to the descending order of ROI-grid size. The steps 1520, 1530 and 1540 are used for copying the individual ROI grid to the second gridded image 1410. The step 1550 checks if all the ROI grids on the gridded image 1360 have been processed. If not, then the steps 1520, 1530 and 1540 are repeated.

Figure 16:
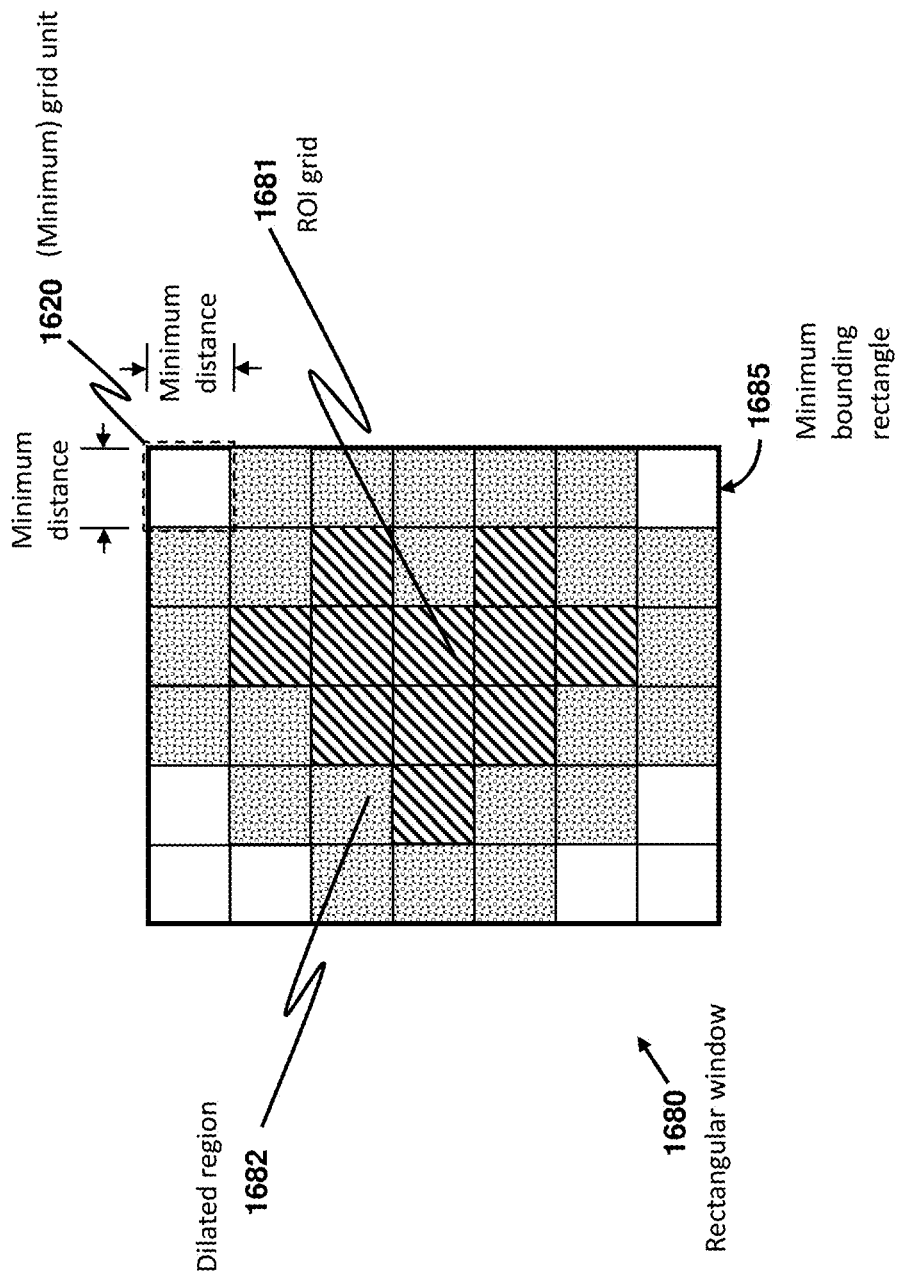
FIG. 16 depicts forming a dilated ROI grid from a ROI grid and subsequently forming a rectangular window when the gridded image has the minimum grid unit.

In the step 1520, the individual ROI grid is dilated by one grid unit to form a dilated ROI grid. FIG. 16 depicts a dilated ROI grid 1683 formed from a ROI grid 1681 for illustrating the step 1520. In FIG. 16, a minimum grid unit 1620 is also shown. The ROI grid 1681 is dilated by one grid unit 1620. That is, the ROI grid 1681 is expanded outward by one grid unit 1620. In FIG. 16, a dilated region 1682 of one grid unit 1620 in width is shown. Augmentation of the ROI grid 1681 and the dilated region 1682 gives a dilated ROI grid 1683. The dilated ROI grid 1683 is then bounded by a minimum bounding rectangle 1685 to form a rectangular window 1680. The rectangular window 1680, which contains (a first copy of) the ROI grid 1681 and has the minimum bounding rectangle 1685 as a perimeter, is used as a sliding window to check if the second gridded image 1410 has an empty space sufficient to house the ROI grid 1681 in the step 1530. For the sake of convenience, the first copy of the ROI grid 1681 is also referenced as the first ROI-grid copy 1681 hereinafter.

In the step 1530, the rectangular window 1680 is slid on the second gridded image 1410 in a raster scanning manner to identify a fitted region on the second gridded image 1410 such that in the fitted region, the first ROI-grid copy 1681 does not overlap with another copy of ROI grid already put on the second gridded image 1410. Raster scanning may be done as follows. The rectangular window 1680 is advanced on the second gridded image 1410 by one grid unit 1620 along the x-direction 11. If after checking it is found that there is overlapping between the first ROI-grid copy 1681 and another ROI-grid copy, advance the rectangular window 1680 by one grid unit 1620 in the x-direction 11 again and repeat the checking. It follows that the rectangular window 1680 travels along a row on the second gridded image 1410. When the rectangular window 1680 reaches an end of the row, the rectangular window 1680 goes to a next row, which is one grid unit 1620 from the original row in the y-direction 12. Instead of doing row-wise raster scanning, it is also possible to use column-wise raster scanning.

In the step 1540, the first ROI-grid copy 1681 is put on the fitted region identified in the step 1530 where there is no overlapping found. Note that a first location of a certain ROI-grid copy on the second gridded image 1410 is same as a second location on the gridded image 1360 for a corresponding original ROI grid to be relocated. Hence, the directed displacement of moving the original ROI grid on the gridded image 1360 can be computed.

A.4.2. Fast Implementation of the Step 1530

Figure 17:
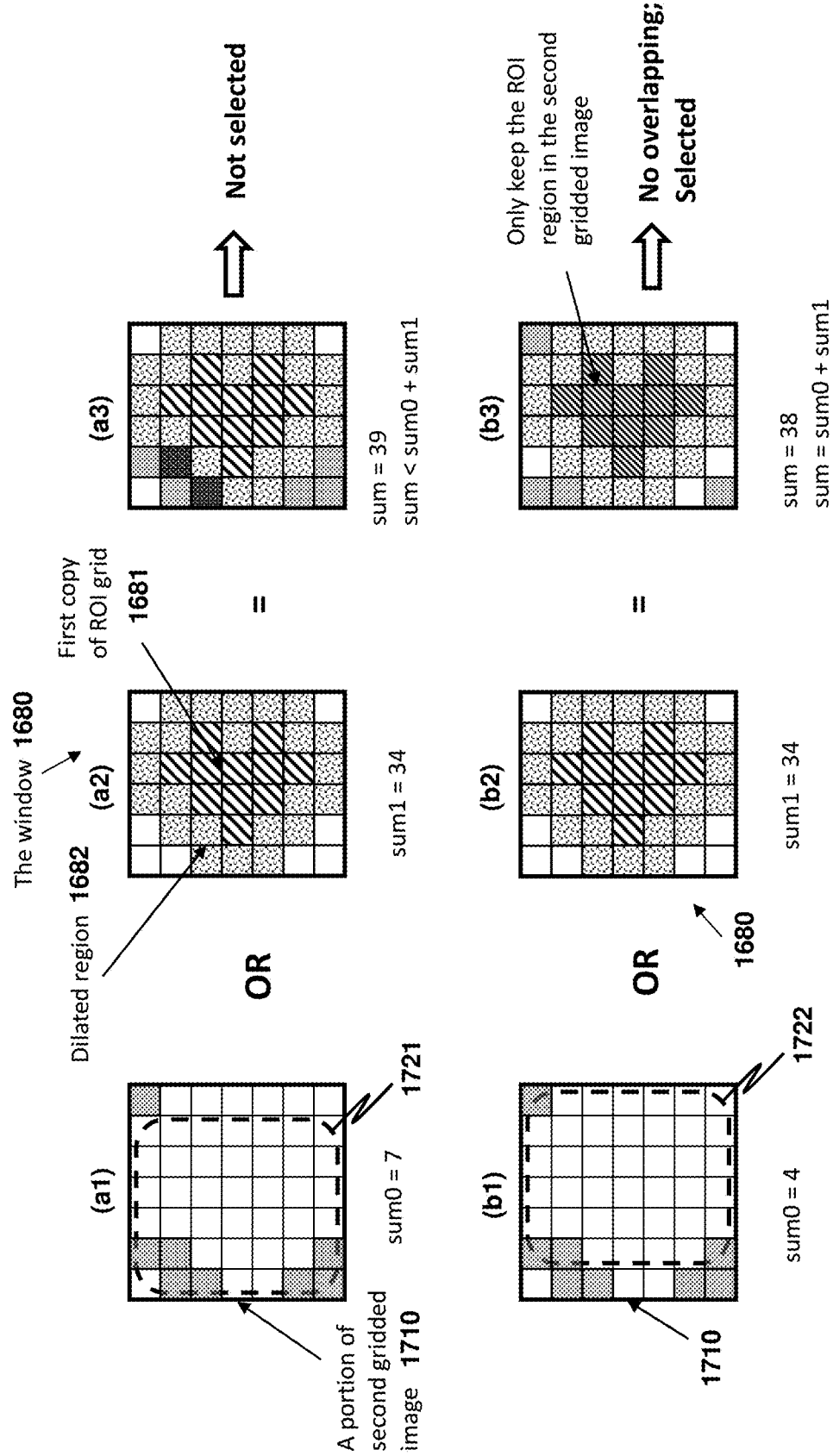
FIG. 17 depicts using the rectangular window of FIG. 16 to identify a fitted region on which the ROI grid can be relocated.

FIG. 17 provides, in accordance with one embodiment of the present invention, a fast computer implementation of the step 1530 in identifying whether there is overlapping between the first ROI-grid copy 1681 and another ROI-grid copy on the second gridded image 1410.

Subplot (a1) of FIG. 17 shows a portion 1710 of second gridded image on which some squares (highlighted) have already been occupied by other ROI-grid copies. On the image portion 1710, the occupied squares are each assigned with a value of 1 while remaining squares with 0. When the rectangular window 1680 is positioned on a first area 1721, the sum of values of squares on the first area 1721 is 7 (indicated as "sum0=7"). Subplot (a2) shows the rectangular window 1680 having the first ROI-grid copy 1681 and the dilated region 1682. Squares in the rectangular window 1680 occupied with either the first ROI-grid copy 1681 or the dilated region 1682 are each assigned a value of 1 while remaining squares are each assigned with a value of 0. The sum of values of the squares in the rectangular window 1680 is 34 (indicated as "sum1=34"). In subplot (a3), the values of squares on the first area 1721 are element-wise Boolean OR-ed with the values of squares in the rectangular window 1680. The sum of resultant values after OR-ing is 39 (indicated as "sum=39"). Since sum<sum0+sum1, it indicates that there is overlapping between the first ROI-grid copy 1681 and at least one ROI-grid copy already on the second gridded image 1410.

In subplot (b1) of FIG. 17, the rectangular window 1680 is advanced and re-positioned on a second area 1722. The sum of values of squares on the second area 1722 is 4 (indicated as "sum0=4"). Subplot (b2) is the same as subplot (a2), so that "sum1=34". Subplot (b3) is obtained by element-wise OR-ing the values of squares on the second area 1722 and the values of squares in the rectangular window 1680. The sum of values in subplot (b3) is 38 (indicated as "sum=38"). Since sum=sum0+sum1, there is no overlapping between the first ROI-grid copy 1681 and any ROI-grid copy on the second gridded image 1410. Only the first ROI-grid copy 1681 is needed to be copied on the second gridded image 1410 (in the step 1540). Note that the distance between the first ROI-grid copy 1681 and other ROI-grid copies already on the second gridded image 1410 is at least the minimum distance in the x- and y-directions 11, 12, thus satisfying the above-mentioned first constraint.

Note that in computer implementation, the rectangular window 1680 and the second gridded image 1410 may be implemented as binary arrays. Only an operation of summing values in each binary array is required. Hence, the method depicted in FIG. 17 is hardware-friendly in computer implementation, requires less memory, and reduces the computation cost and required power.

Figure 18:
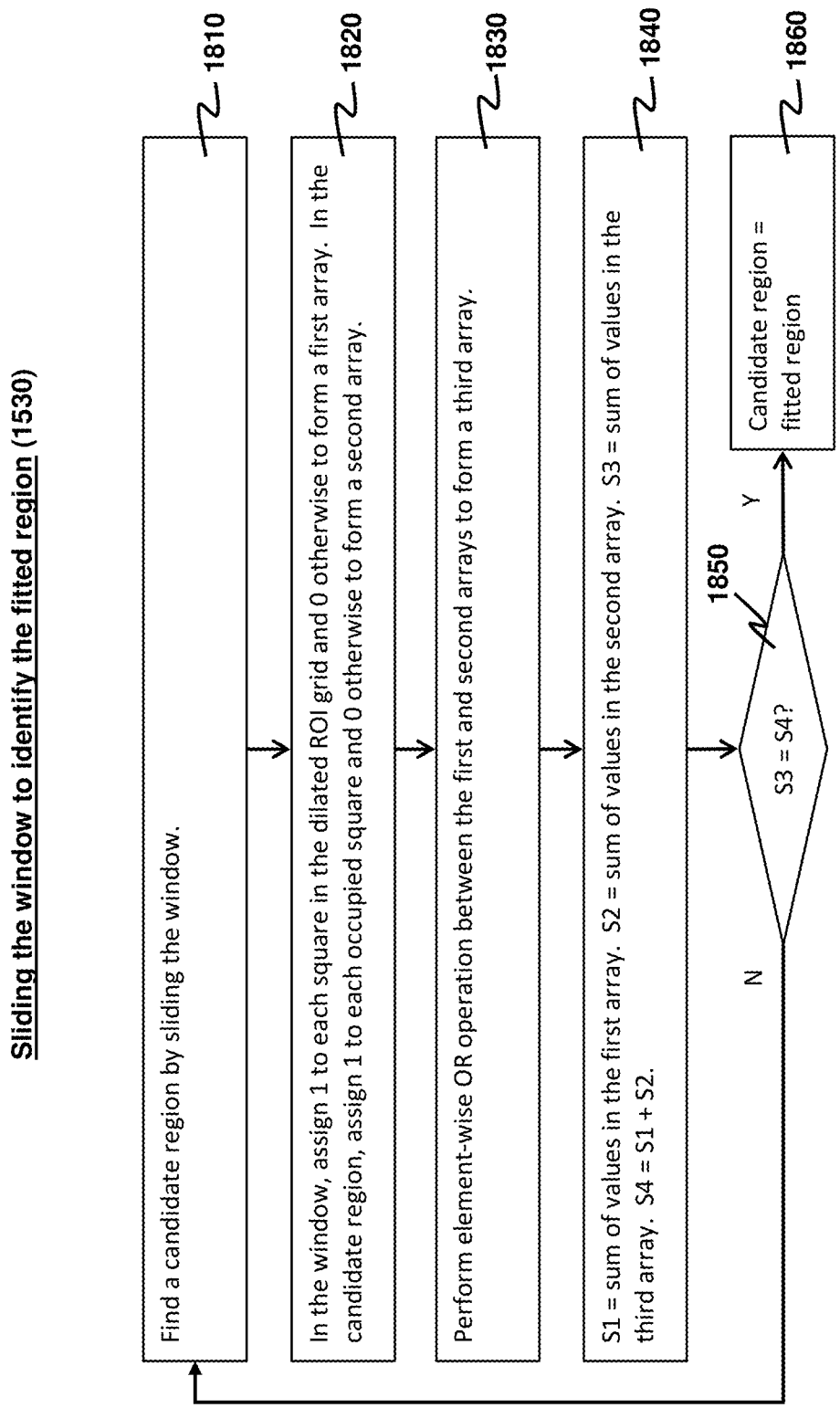
FIG. 18 depicts a flowchart showing, in accordance with one embodiment of the present invention, a process of identifying the fitted region according to the approach given by FIG. 17.

According on the approach made in FIG. 17, FIG. 18 depicts, in accordance with one embodiment of the present invention, a flowchart showing an identifying process for performing the step 1530 of sliding the rectangular window 1680 on the second gridded image 1410 to identify a fitted region. For the identifying process to be elaborated, it is considered that the fitted region has a size of the rectangular window 1680.

In the identifying process, a candidate region on the second gridded image 1410 is selected as a candidate of the fitted region (step 1810). According to the step 1530, the candidate region is selected by sliding the rectangular window 1680 on the second gridded image 1410 in a raster scanning manner The candidate region has the size of the rectangular window 1680. As an example, the first area 1721 or the second area 1722 on the second gridded image 1410 may be selected as the candidate region. Whether the selected candidate region is the fitted region is then determined.

On the rectangular window 1680, each square occupied by the dilated ROI grid 1683 is assigned with a value of 1, and each remaining square is assigned with a value of 0 (step 1820). A first array of values assigned to the rectangular window 1680 is obtained.

On the candidate region, each square occupied by any ROI-grid copy already on the second gridded image 1410 is assigned with a value of 1, and each remaining square is assigned with a value of 0 (the step 1820). A second array of values assigned to the candidate region is obtained.

In a step 1830, an element-wise Boolean OR operation between the first array of values and the second array of values is performed to yield a third array of values.

In a step 1840, compute: a first sum, S1, by summing the values in the first array; a second sum, S2, by summing the values in the second array; a third sum, S3, by summing the values in the third array; and a fourth sum, S4, by adding the first sum and the second sum together.

In a step 1850, whether the candidate region is the fitted region is determined by checking if the third sum equals to the fourth sum. If S3=S4, the candidate region is determined to be the fitted region (step 1860). If not, the candidate region is not the fitted region. Then another candidate region is selected and checked whether this candidate region is the fitted region by repeating the steps 1810, 1820, 1830, 1840 and 1850. In the step 1810, a next candidate region is generally selected to be one grid unit 1620 offset from the original candidate region.

A.5. Gridded Image with a Non-Minimum Grid Unit

As used herein, a non-minimum grid unit is a grid unit that is not a minimum grid unit. As mentioned above, the grid unit 1320 has the width 1318 and the height 1319 each being at least the minimum distance. Thus, the non-minimum grid unit is a rectangle having two adjacent sides satisfying that 1) each of the two adjacent sides is at least the minimum distance in length, and 2) at least one of the two adjacent sides is strictly longer than the minimum distance.

The above-mentioned procedures described for FIGS. 15 and 18 are applicable to relocating the ROI grids on the gridded image 1360 when the grid unit 1320 is a non-minimum grid unit, provided the grid 1325 is modified from being an evenly spaced one to an unevenly spaced one as illustrated hereinafter.

Figure 19:
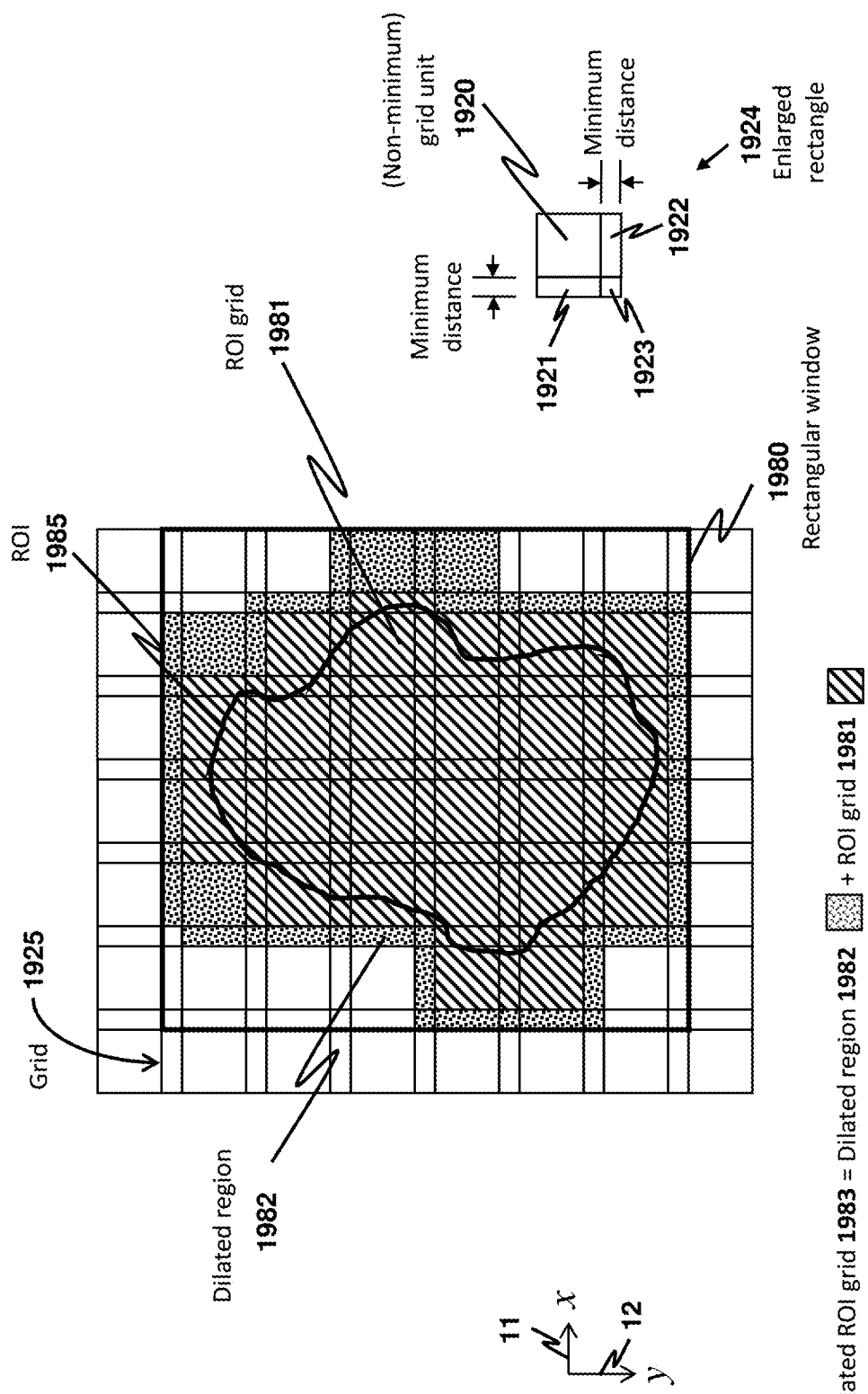
FIG. 19 depicts forming a dilated ROI grid from a ROI grid and subsequently forming a rectangular window when the gridded image has a non-minimum grid unit, namely, a rectangle having two adjacent sides satisfying that 1) each of the two adjacent two sides is at least the minimum distance in length, and 2) at least one of the two adjacent sides is strictly longer than the minimum distance.

FIG. 19 depicts a ROI grid 1981 and a dilated ROI grid 1983 both formed from a ROI 1985 for illustrating the step 1520. FIG. 19 corresponds to FIG. 16 except that a non-minimum grid unit 1920 is used. First, a grid 1925 is formed by repeating in both the x- and y-directions 11, 12 an enlarged rectangle 1924 formed by augmenting the non-minimum grid unit 1920 and three minor grid units 1921-1923 where the three minor grid units 1921-1923 collectively form an L-shape portion that accommodates the non-minimum grid unit 1920. In each of the three minor grid units 1921-1923, at least one side has a length of the minimum distance. Therefore, each side of the enlarged rectangle 1924 is extended from the non-minimum grid unit 1920 by a distance of the minimum distance. Also note that the grid 1925 is composed of plural rectangles having more than one size. Second, the ROI 1985 is gridded according to the grid 1925 to form the ROI grid 1981. The ROI grid 1981 is expanded outward by one immediately-adjacent grid unit to from the dilated ROI grid 1983. In FIG. 19, the dilated ROI grid 1983 is formed by combining the original ROI grid 1981 and a dilated region 1982. A rectangular window 1980 that minimally bounds the dilated ROI grid 1983 is created.

With the dilated ROI grid 1983 that is obtained according to the aforementioned way, the same procedure described for FIG. 15 is used to implement the step 1220 for relocating the ROI grids on the gridded image 1360.

Figure 20:
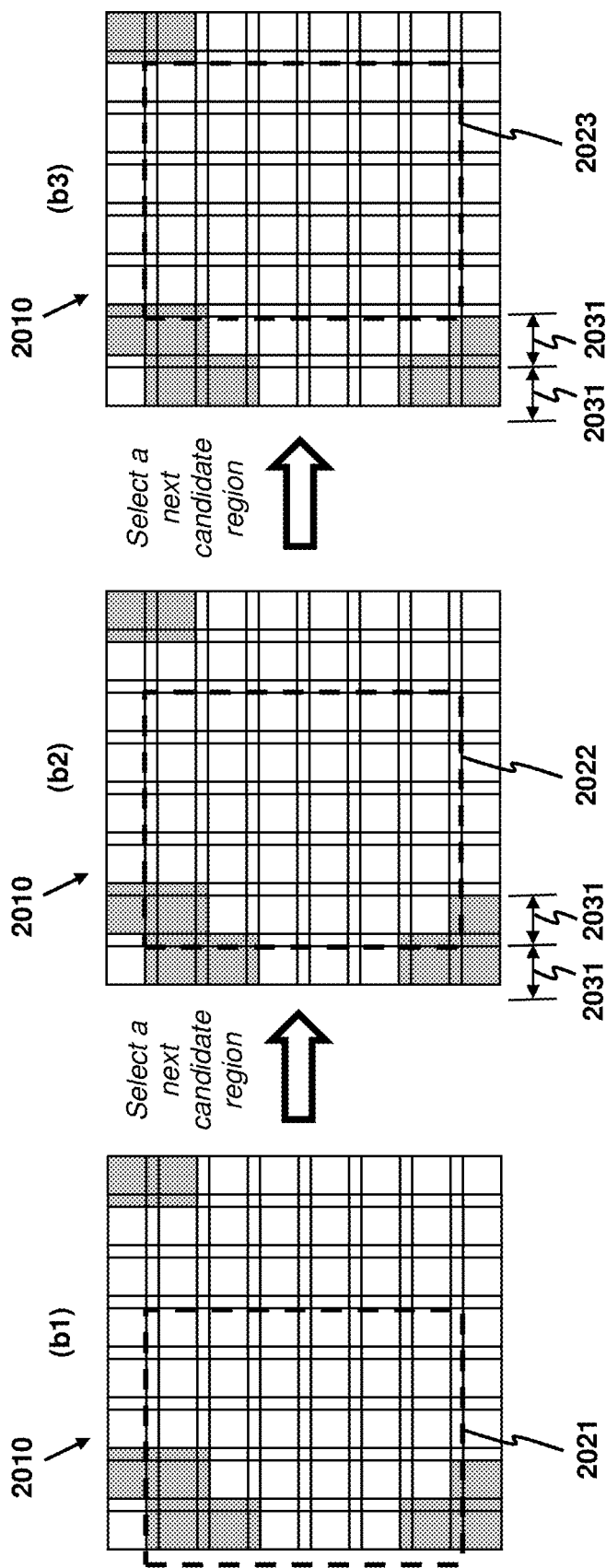
FIG. 20 depicts using the rectangular window of FIG. 19 to identify a fitted region on which the ROI grid can be relocated.
Figure 20:
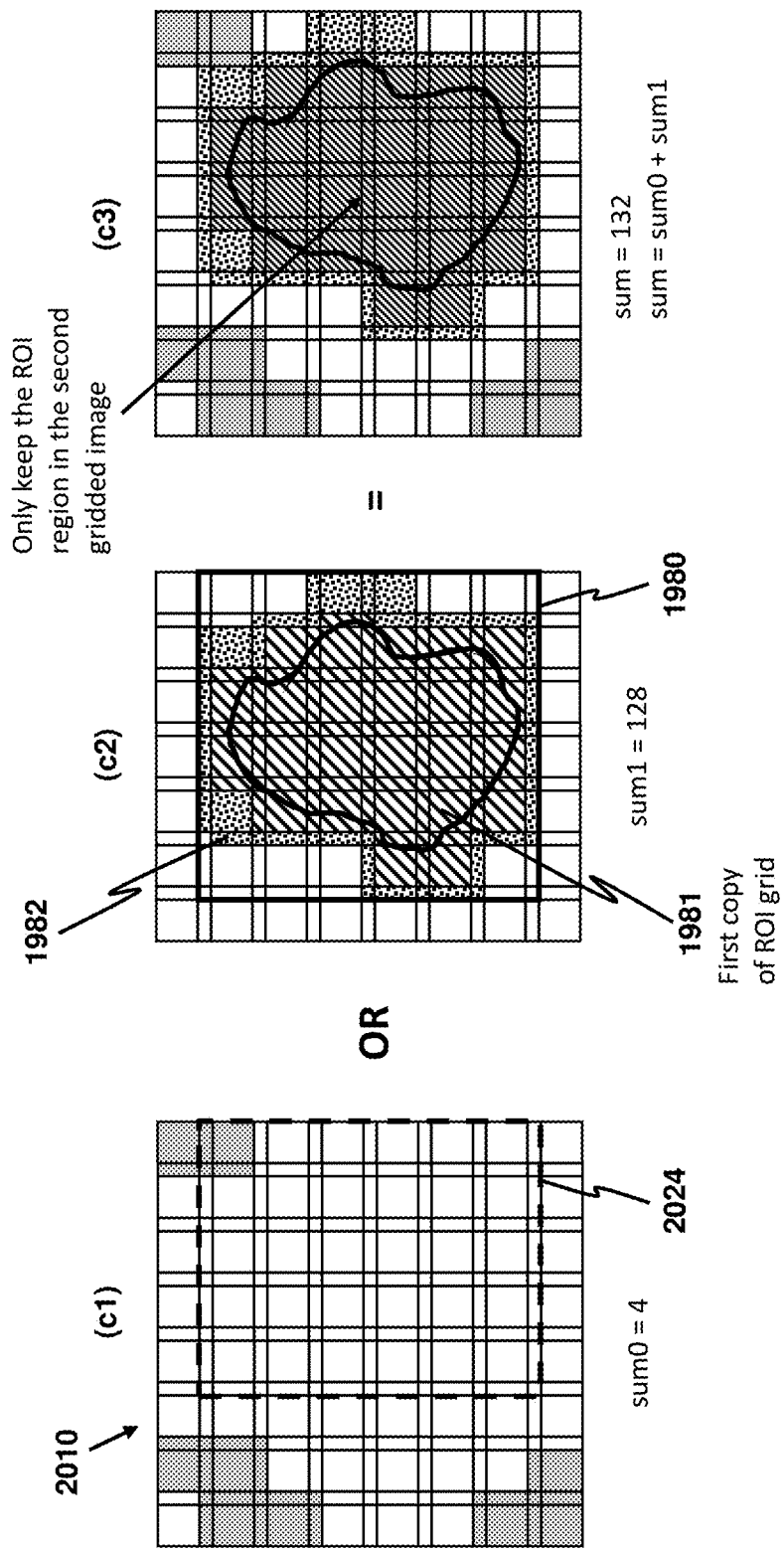

The above-mentioned procedure described for FIG. 18 is also used for fast implementation of the step 1530 although selecting a next candidate region in the step 1810 may be slightly different from the previous case of using a minimum grid unit. For convenience, a first copy of the ROI grid 1981 is also referenced as the first ROI-grid copy 1981 hereinafter. In the step 1530, the rectangular window 1980 is slid on the second gridded image 1410 in a raster scanning manner to identify a fitted region on the second gridded image 1410 such that in the fitted region, the first ROI-grid copy 1981 does not overlap with another copy of ROI grid already put on the second gridded image 1410. FIG. 20, similar to FIG. 17, illustrates a fast computer implementation of the step 1530 in identifying whether there is overlapping between the first ROI-grid copy 1981 and another ROI-grid copy on the second gridded image 1410.

Subplot (a1) of FIG. 20 shows a portion 2010 of second gridded image on which some rectangles (highlighted) have already been occupied by other ROI-grid copies. On the image portion 2010, the occupied rectangles are each assigned with a value of 1 while remaining rectangles with 0. When the rectangular window 1980 is positioned on a first area 2021, the sum of values of rectangles on the first area 2021 is 23 (indicated as "sum0=23"). Subplot (a2) shows the rectangular window 1980 having the first ROI-grid copy 1981 and the dilated region 1982. Rectangles in the rectangular window 1980 occupied with either the first ROI-grid copy 1981 or the dilated region 1982 are each assigned a value of 1 while remaining rectangles are each assigned with a value of 0. The sum of values of the rectangles in the rectangular window 1980 is 128 (indicated as "sum1=128"). In subplot (a3), the values of rectangles on the first area 2021 are element-wise Boolean OR-ed with the values of rectangles in the rectangular window 1980. The sum of resultant values after OR-ing is 138 (indicated as "sum=138"). Since sum<sum0+sum1, it indicates that there is overlapping between the first ROI-grid copy 1981 and at least one ROI-grid copy already on the second gridded image 1410.

The selection of a next candidate region in the step 1810 after the step 1850 determines that a candidate region is not a fitted region follows an approach illustrated in subplots (b1), (b2) and (b3) of FIG. 20. In subplot (b1), the first area 2021 is the original candidate region. Since the first area 2021 is not the fitted region as there is potential ROI-grid overlapping, the next candidate region is selected. In subplot (b2), a second area 2022 is selected to be the next candidate region. The second area 2022 is not one immediately-adjacent grid unit offset from the first area 2021, but is away from the first area by a side length 2031 of the enlarged rectangle 1924. In general, the next candidate region is distant from the original candidate region by a multiple of the side length 2031. It can be shown that the second area 2022 is still not the fitted region. In subplot (b3), the next candidate region is selected to be a third area 2023, which is one side length 2031 from the second area 2022. It can also be shown that the third area 2023 is not the fitted region too.

In subplot (c1), the rectangular window 1980 is advanced and re-positioned on a fourth area 2024 as the next candidate region. The sum of values of rectangles on the fourth area 2024 is 4 (indicated as "sum0=4"). Subplot (c2) is the same as subplot (a2), so that "sum1=128". Subplot (c3) is obtained by element-wise OR-ing the values of rectangles on the fourth area 2024 and the values of rectangles in the rectangular window 1980. The sum of values in subplot (c3) is 132 (indicated as "sum=132"). Since sum=sum0+sum1, there is no overlapping between the first ROI-grid copy 1981 and any ROI-grid copy on the second gridded image 1410. Only the first ROI-grid copy 1681 is needed to be copied on the second gridded image 1410 (in the step 1540). Note that the distance between the first ROI-grid copy 1981 and other ROI-grid copies already on the second gridded image 1410 is at least the minimum distance in the x- and y-directions 11, 12, thus satisfying the above-mentioned first constraint.

A.6. Rotating the ROIs Before Relocation in Rearranging the ROIs (Step 410)

In the step 410, it is possible to pack the ROIs further closer by properly rotating the ROIs before relocation is made. There are two possible strategies. One is to rotate the whole testing image and the other is to individually rotate each ROI with an optimized angle.

In the strategy of rotating the whole testing image, mapping between an original ROI and a rotated one is simple. The angle of rotating the testing image is generally determined according to an optimized angle in rotating a major ROI on the testing image. In computer implementation of this strategy, computation required is not much. However, there is a disadvantage that a universal rotation angle has a limited boost on more-closely packing the ROIs.

In another strategy of individual rotating each ROI, the amount of computation involved is much greater than the first strategy of rotating the whole testing image. However, the ROIs are more closely packed in the compacted testing image in comparison to the first strategy.

Figure 21:
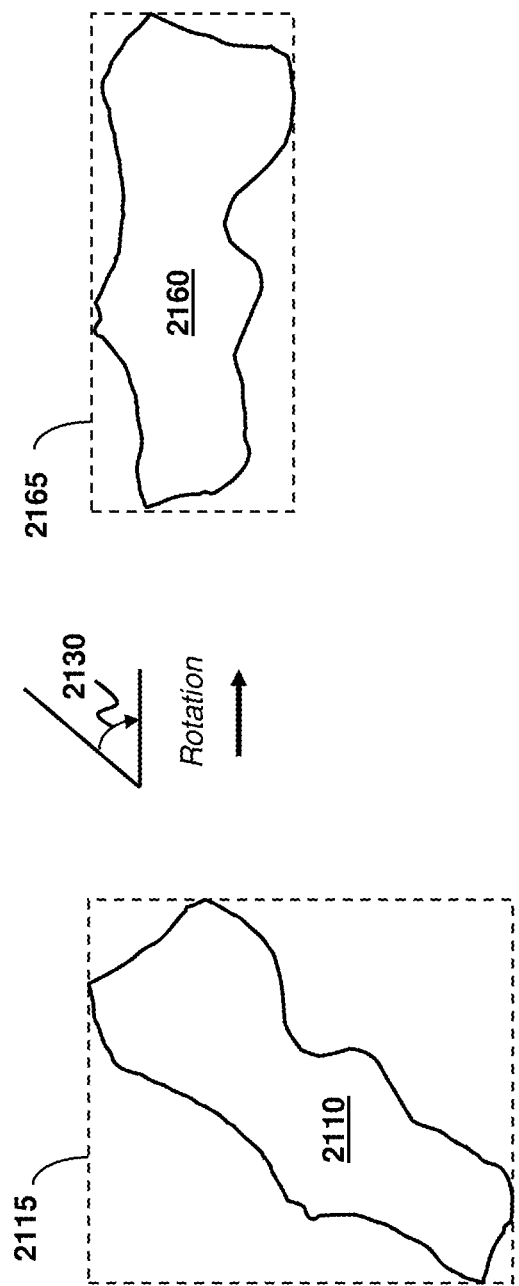
FIG. 21 depicts one approach of determining an optimized angle for rotating an original ROI before relocation in order to have the ROIs packs more closely together.

In both strategies, there is a need to determine an optimized rotation angle for a certain ROI. FIG. 21 depicts one approach of determining the optimized rotation angle. Consider an original ROI 2110. A first minimum bounding rectangle 2115 is used to bound the original ROI 2110. If the original ROI 2110 is rotated by an angle 2130, a rotated ROI 2160 is formed. A second minimum bounding rectangle 2165 is used to bound the rotated ROI 2160. A higher packing efficiency is obtained by reducing an area not occupied by the rotated ROI 2160 as much as possible. Hence, an optimized angle for rotating the original ROI 2110 can be found by finding the angle 2130 among all possible angles such that an area of the second minimum bounding rectangle 2165 is minimized B. Disclosed System A second aspect of the present invention is to provide a system that employs a FCN to classify plural cells into normal and abnormal cells according to the method disclosed above as set forth in the first aspect of the present invention. The FCN has plural convolutional layers each having a respective value of stride. The system is used for cancer-cell screening and/or precancerous-abnormality screening. Particularly, the system includes a specialized processor having a hardware configuration optimized for computing plural convolutional products in parallel for an image. The specialized processor is used for implementing the FCN.

Figure 22:
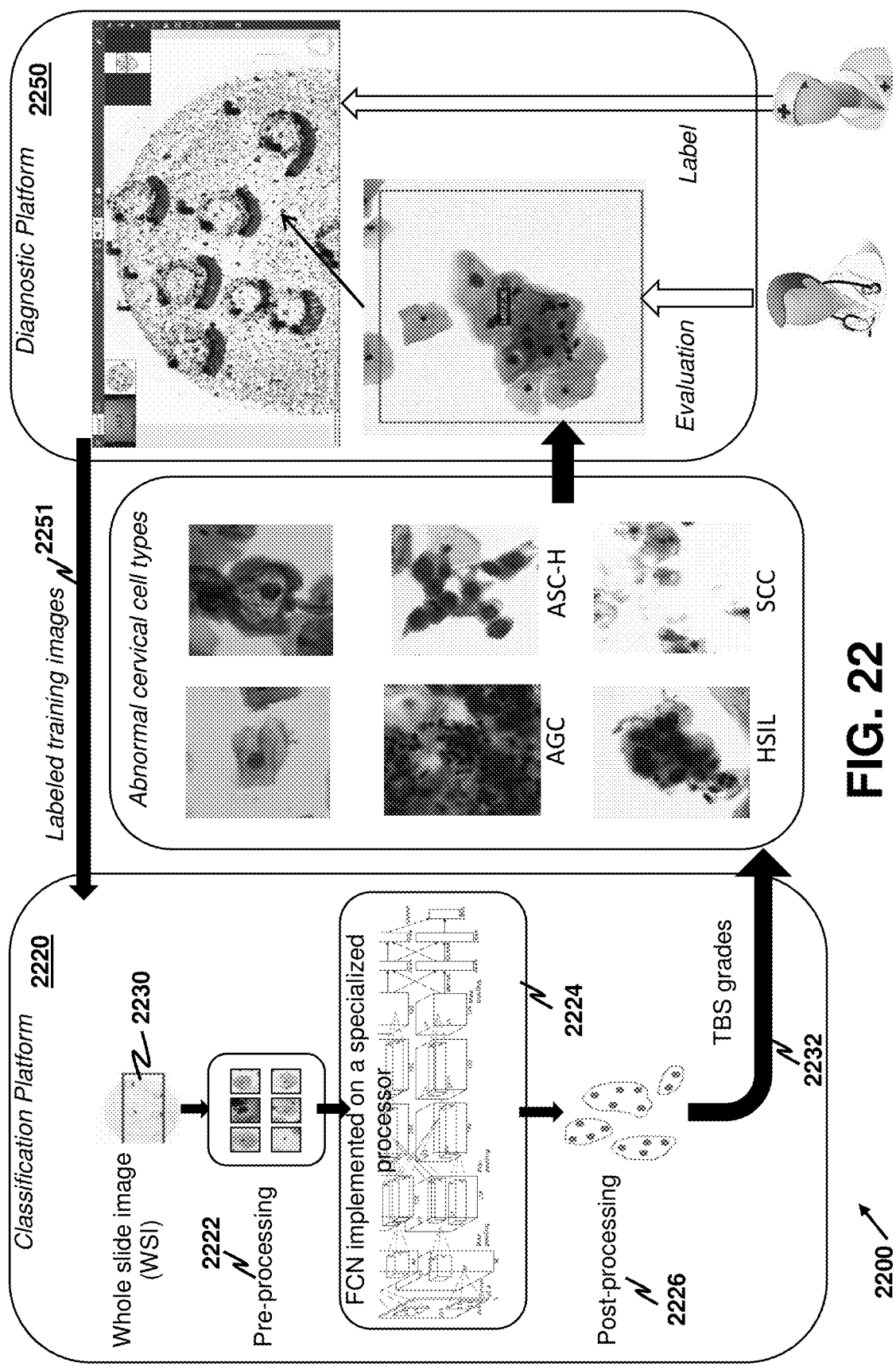
FIG. 22 depicts a schematic structure of an exemplary system for cervical cancer-cell screening and/or precancerous-abnormality screening, where the system employs the disclosed method to speed up cell classification.

Exemplarily, the system is illustrated with the aid of FIG. 22, which depicts a schematic structure of a system 2200 designed for diagnosing cervical cancer and detecting precancerous abnormalities appeared in a cervix. The system 2200 comprises a diagnostic platform 2250 and a classification platform 2220.

The diagnostic platform 2250 is a first computing subsystem that interacts with medical practitioners and allows the medical practitioners to classify and label a (limited) number of cells for FCN training. For FCN training, the set of cell types that are of interest to cervical-cancer diagnosis includes a non-abnormal object and one or more abnormal cells. The one or more abnormal cells may include one or more of the following: LSIL, HSIL, AGC, ASC-US, ASC-H, SCC, AIS and ADC. As a result, labeled training images 2251 are obtained and sent to the classification platform 2220. A FCN 2224, implemented on a specialized processor having an optimized hardware configuration as mentioned above, is trained with the labeled training images 2251 for deep learning.

The classification platform 2220 is a second computing subsystem used for classifying the cells into normal and abnormal cells.

The classification platform 2220 first obtains a WSI 2230 of a slide that contains a plurality of cells for cervical cancer-cell screening or precancerous-abnormality screening. The plurality of cells on the slide is originally obtained from a cervix of a patient.

Pre-processing 2222 of the WSI 2230 is performed by executing a pre-processing process. In the pre-processing process, the WSI is segmented into a background and plural ROIs according to any of the disclosed embodiments of the step 310 taken the WSI as the testing image. After the background and the ROIs are identified and geometrically characterized, the testing image is compacted to form a compacted testing image in accordance with any embodiment of the step 330 as disclosed above. Prior to compacting the testing image, the background of the testing image may be replaced by a blank one for background purification in accordance with a disclosed embodiment of the step 320. The compacted testing image is sent to the FCN 2224 for cell classification.

The FCN 2224 classifies the plurality of cells on the testing image to yield a plurality of classification results. As the compacted testing image rather than the original testing image is used by the FCN 2224 in cell classification, it leads to a reduction in a computation time required to accomplish classification of the plurality of cells without a need for re-optimizing the hardware configuration of the specialized processor.

Post-processing 2226 of the plurality of classification results is carried out to yield TBS grades 2232. TBS is a system commonly used for reporting Pap smear results in cervical or vaginal cytologic diagnoses. For details of TBS and TBS grades, see, e.g., R. Nayar and D. C. Wilbur, *The Bethesda System for Reporting Cervical Cytology*, Springer, 2015.

Except the FCN 2224, which is implemented on the above-mentioned specialized processor with the optimized hardware configuration, each of the first and second computing systems mentioned above may be realized by general-purpose computers, specialized computers, computing servers, one or more computing processors with data storing devices, etc. The aforesaid computing processors may be general-purpose processors, or specialized processors with optimization in one or more certain aspects.

C. Remarks

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A method for classifying a plurality of cells imaged on a testing image by using a fully convolutional network (FCN), the FCN having plural convolutional layers each having a respective value of stride, the FCN being implemented on a specialized processor having a hardware configuration optimized for computing plural convolutional products in parallel for an image, the method comprising:

segmenting the testing image into a background and plural regions of interest (ROIs), an individual ROI comprising one or more connected individual cells disjoint from remaining cells in the plurality of cells;

compacting the testing image to form a compacted testing image, including:

rearranging the ROIs for packing the ROIs closer together under a first constraint that any adjacent two of the rearranged ROIs are separated in each of x- and y-directions of the testing image by a distance in pixel not less than a minimum distance determined according to the stride values of the convolutional layers, wherein an individual ROI is rearranged by performing one or more geometric operations without resizing the individual ROI, the one or more geometric operations including relocating the individual ROI; and enclosing an entirety of rearranged ROIs with a boundary to form the compacted testing image, wherein the boundary is a perimeter of the compacted testing image and is selected under a second constraint that a first number of pixels occupied by the compacted testing image is less than a second number of pixels occupied by the testing image; and classifying the plurality of cells by processing the compacted testing image rather than the original testing image with the FCN for reducing a time required to accomplish the classifying of the plurality of cells without a need for re-optimizing the hardware configuration.

2. The method of claim 1, wherein the minimum distance, $d_{min}$, is given by $d_{min} = \frac{1}{2} \Pi_{i=1}^{N} \varphi_i$ where N is a total number of the convolutional layers, and $\varphi_i$ is the stride value of ith convolutional layer.

3. The method of claim 1 further comprising:

before the testing image is compacted, replacing the background with a blank one in the testing image for minimizing interference due to the background in the classifying of the plurality of cells.

4. The method of claim 1, wherein the boundary is a rectangular boundary.

5. The method of claim 4, wherein the rectangular boundary has a width and a length measured in pixel, each of the width and length being selected to be minimally sufficient to enclose all the rearranged ROIs.

6. The method of claim 4, wherein the rectangular boundary has a width and a length measured in pixel, each of the width and length being selected to be minimally sufficient to enclose all the rearranged ROIs while satisfying one or more image-size requirements of the FCN in processing the compacted testing image.

7. The method of claim 1, wherein:
the segmenting of the testing image into the background and the ROIs includes determining a location and a contour of each of the ROIs on the testing image; and
the rearranging of the ROIs includes:
gridding the testing image with a grid unit to form a gridded image, wherein the individual ROI is mosaicked to form a corresponding ROI grid on the gridded image, whereby plural ROI grids are formed on the gridded image;
relocating the ROI grids on the gridded image one by one according to a descending order of ROI-grid size under a third constraint that the ROI grids after relocation do not overlap; and
in relocating the corresponding ROI grid on the gridded image with a directed displacement, relocating the individual ROI on the testing image with the same directed displacement.

8. The method of claim 7, wherein the grid unit is a minimum grid unit.

9. The method of claim 7, wherein the relocating of the ROI grids on the gridded image one by one according to the descending order of ROI-grid size under the third constraint comprises:
creating a second gridded image having a dimension of the gridded image and being empty when created;
copying the ROI grids one by one to the second gridded image according to the descending order of ROI-grid size, wherein the copying of said corresponding ROI grid to the second gridded image includes:
dilating said corresponding ROI grid by one grid unit to form a dilated ROI grid;
bounding the dilated ROI grid with a minimum bounding rectangle to form a rectangular window, wherein the rectangular window contains a first copy of said corresponding ROI grid;
sliding the rectangular window on the second gridded image in a raster scanning manner along an x- or y-direction to identify a fitted region on the second gridded image such that in the fitted region, said first copy does not overlap with another ROI-grid copy already on the second gridded image; and
putting said first copy on the fitted region, whereby a first location of said first copy on the second gridded image is same as a second location on the gridded image for said corresponding ROI grid to be relocated, thereby allowing the directed displacement to be determined; and
relocating said corresponding ROI grid to the second location on the gridded image.

10. The method of claim 9, wherein the fitted region has a size of the rectangular window, and the fitted region is identified by an identifying process that includes determining whether a candidate region on the second gridded image is the fitted region, the candidate region having the size of the rectangular window, the determining of whether the candidate region is the fitted region comprising:
on the rectangular window, assigning each of squares occupied by the dilated ROI grid with a value of 1, and each of remaining squares a value of 0, whereby a first array of values assigned to the rectangular window is obtained;
on the candidate region, assigning each of squares occupied by any ROI-grid copy already on the second gridded image with a value of 1, and each of remaining squares a value of 0, whereby a second array of values assigned to the candidate region is obtained;
performing an element-wise Boolean OR operation between the first array of values and the second array of values to yield a third array of values;
computing a first sum by summing the values in the first array;
computing a second sum by summing the values in the second array;
computing a third sum by summing the values in the third array;
computing a fourth sum by adding the first sum and the second sum together;
responsive to finding that the third sum is equal to the fourth sum, assigning the candidate region as the fitted region, whereby the fitted region is identified; and
responsive to finding that the third sum is not equal to the fourth sum, declaring that the candidate region is not the fitted region.

11. The method of claim 1, wherein the one or more geometric operations further include rotating the individual ROI before relocation.

12. The method of claim 1, wherein:
the testing image is a color one having plural color channels, each of the color channels having respective luminance data; and
the segmenting of the testing image into the background and the ROIs includes:
determining a threshold of luminance value for differentiating the ROIs from the background on the testing image;
performing thresholding on each of the color channels according to the determined threshold to yield a respective binary image, whereby plural binary images for the color channels are obtained;
performing a pixel-wise Boolean operation on the binary images to yield a mask, each pixel of the mask taking either a first value or a second value, the mask comprising islands of the first value, whereby an individual island on the mask corresponds to a respective ROI on the testing image, and a remaining part of the mask other than the islands corresponds to the background;
filtering the mask for incorporating into the individual island any group of one or more pixels completely surrounded by the individual island and taken the second value; and
determining a location and a contour of the individual island such that the determined location and contour of the individual island are a location and a contour of the respective ROI on the testing image.

13. The method of claim 12, wherein:
the determining of the threshold comprises the steps of:
(a) generating a respective histogram distribution of luminance data for each color channel, whereby plural histogram distributions for all the color channels are obtained;
(b) for each color channel, identifying a first luminance value at which a highest peak in the respective histogram distribution occurs, and a second luminance value at which a trough immediately adjacent to the highest peak occurs, wherein the second luminance value is less than the first luminance value, whereby the second luminance values identified for the color channels are obtained;

(c) determining whether a first condition is satisfied, wherein the first condition is that the second luminance values are greater than a limit predetermined for preventing occurrence of an overly-low threshold unsafe for being used in segmenting the testing image;

(d) responsive to determining that the first condition is satisfied, setting the threshold according to a minimum one of the second luminance values;

(e) responsive to determining that the first condition is not satisfied, performing the steps (f)-(h);

(f) for each color channel, identifying a third luminance value at which a second highest peak in the respective histogram distribution occurs, whereby the third luminance values identified for the color channels are obtained; and (h) setting the threshold according to a minimum one of the third luminance values.

14. The method of claim 1, wherein the segmenting of the testing image into the background and the ROIs includes:
creating a grayscale testing image having luminance data of the testing image;
determining a threshold of luminance value for differentiating the ROIs from the background on the testing image, wherein the threshold is a mean value of luminance data of the grayscale testing image;
performing thresholding on the grayscale testing image according to the determined threshold to yield a mask, each pixel of the mask taking either a first value or a second value, the mask comprising islands of the first value, whereby an individual island on the mask corresponds to a respective ROI on the testing image, and a remaining part of the mask other than the islands corresponds to the background; and
determining a location and a contour of an individual island such that the determined location and contour of the individual island are a location and a contour of the respective ROI on the testing image.

15. The method of claim 1, wherein the plurality of cells is originally obtained for cancer-cell screening or precancerous-abnormality screening.

16. A system for classifying a plurality of cells imaged on a testing image, the system comprising:
a first processor that is a specialized processor having a hardware configuration optimized for computing plural convolutional products in parallel for an image, the first processor being used for implementing a fully convolutional network (FCN), the FCN having plural convolutional layers each having a respective value of stride, the FCN being used for classifying the plurality of cells; and
a second processor configured to execute a process for pre-processing the testing image before the plurality of cells is classified;
wherein the pre-processing process comprises:
segmenting the testing image into a background and plural regions of interest (ROIs), an individual ROI comprising one or more connected individual cells disjoint from remaining cells in the plurality of cells;
compacting the testing image to form a compacted testing image, including:
rearranging the ROIs for packing the ROIs closer together under a first constraint that any adjacent two of the rearranged ROIs are separated in each of x- and y-directions of the testing image by a distance in pixel not less than a minimum distance determined according to the stride values of the convolutional layers, wherein an individual ROI is rearranged by performing one or more geometric operations without resizing the individual ROI, the one or more geometric operations including relocating the individual ROI; and
enclosing an entirety of rearranged ROIs with a boundary to form the compacted testing image, wherein the boundary is a perimeter of the compacted testing image and is selected under a second constraint that a first number of pixels occupied by the compacted testing image is less than a second number of pixels occupied by the testing image; and
sending the compacted testing image rather than the original testing image to the first processor for classifying the plurality of cells by the FCN, thereby reducing a time required to accomplish the classifying of the plurality of cells without a need for re-optimizing the hardware configuration.

17. The system of claim 16, wherein the minimum distance, $d_{min}$, is given by $d_{min}=\frac{1}{2}\Pi_{i=1}^{N}\varphi_i$ where N is a total number of the convolutional layers, and $\varphi_i$ is the stride value of ith convolutional layer.

18. The system of claim 16, wherein the pre-processing process further comprises:
before the testing image is compacted, replacing the background with a blank one in the testing image for minimizing interference due to the background in the classifying of the plurality of cells.

19. The system of claim 16, wherein the boundary is a rectangular boundary.

20. The system of claim 19, wherein the rectangular boundary has a width and a length measured in pixel, each of the width and length being selected to be minimally sufficient to enclose all the rearranged ROIs.

21. The system of claim 19, wherein the rectangular boundary has a width and a length measured in pixel, each of the width and length being selected to be minimally sufficient to enclose all the rearranged ROIs while satisfying one or more image-size requirements of the FCN in processing the compacted testing image.

22. The system of claim 16, wherein:
the segmenting of the testing image into the background and the ROIs includes determining a location and a contour of each of the ROIs on the testing image; and
the rearranging of the ROIs includes:
gridding the testing image with a grid unit to form a gridded image, wherein the individual ROI is mosaicked to form a corresponding ROI grid on the gridded image, whereby plural ROI grids are formed on the gridded image;
relocating the ROI grids on the gridded image one by one according to a descending order of ROI-grid size under a third constraint that the ROI grids after relocation do not overlap; and
in relocating the corresponding ROI grid on the gridded image with a directed displacement, relocating the individual ROI on the testing image with the same directed displacement.

23. The system of claim 22, wherein the relocating of the ROI grids on the gridded image one by one according to the descending order of ROI-grid size under the third constraint comprises:

creating a second gridded image having a dimension of the gridded image and being empty when created;

copying the ROI grids one by one to the second gridded image according to the descending order of ROI-grid size, wherein the copying of said corresponding ROI grid to the second gridded image includes:

dilating said corresponding ROI grid by one grid unit to form a dilated ROI grid;

bounding the dilated ROI grid with a minimum bounding rectangle to form a rectangular window, wherein the rectangular window contains a first copy of said corresponding ROI grid;

sliding the rectangular window on the second gridded image in a raster scanning manner along an x- or y-direction to identify a fitted region on the second gridded image such that in the fitted region, said first copy does not overlap with another ROI-grid copy already on the second gridded image; and putting said first copy on the fitted region, whereby a first location of said first copy on the second gridded image is same as a second location on the gridded image for said corresponding ROI grid to be relocated, thereby allowing the directed displacement to be determined; and relocating said corresponding ROI grid to the second location on the gridded image.

24. The system of claim 23, wherein the fitted region has a size of the rectangular window, and the fitted region is identified by an identifying process that includes determining whether a candidate region on the second gridded image is the fitted region, the candidate region having the size of the rectangular window, the determining of whether the candidate region is the fitted region comprising:

on the rectangular window, assigning each of squares occupied by the dilated ROI grid with a value of 1, and each of remaining squares a value of 0, whereby a first array of values assigned to the rectangular window is obtained;

on the candidate region, assigning each of squares occupied by any ROI-grid copy already on the second gridded image with a value of 1, and each of remaining squares a value of 0, whereby a second array of values assigned to the candidate region;

performing an element-wise Boolean OR operation between the first array of values and the second array of values to yield a third array of values;

computing a first sum by summing the values in the first array;

computing a second sum by summing the values in the second array;

computing a third sum by summing the values in the third array;

computing a fourth sum by adding the first sum and the second sum together;

responsive to finding that the third sum is equal to the fourth sum, assigning the candidate region as the fitted region, whereby the fitted region is identified; and responsive to finding that the third sum is not equal to the fourth sum, declaring that the candidate region is not the fitted region.

25. The system of claim 16, wherein the one or more geometric operations further include rotating the individual ROI before relocation.

* * * * *